US007501397B2

(12) United States Patent
Wolfe

(10) Patent No.: US 7,501,397 B2
(45) Date of Patent: Mar. 10, 2009

(54) HELICAL PEPTIDOMIMETICS WITH ENHANCED ACTIVITY

(75) Inventor: Michael S. Wolfe, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 101 days.

(21) Appl. No.: 11/145,573

(22) Filed: Jun. 3, 2005

(65) Prior Publication Data

US 2005/0272659 A1 Dec. 8, 2005

Related U.S. Application Data

(60) Provisional application No. 60/576,965, filed on Jun. 4, 2004.

(51) Int. Cl.
*A61K 38/10* (2006.01)
(52) U.S. Cl. ............................ 514/14; 514/15; 530/327; 530/326
(58) Field of Classification Search ........................ None
See application file for complete search history.

(56) References Cited

U.S. PATENT DOCUMENTS

| | | | |
|---|---|---|---|
| 5,039,660 A | 8/1991 | Leonard | |
| 5,604,198 A | 2/1997 | Poduslo et al. | |
| 5,827,819 A | 10/1998 | Yatvin et al. | |
| 5,919,815 A | 7/1999 | Bradley et al. | |
| 5,955,459 A | 9/1999 | Bradley et al. | |
| 5,977,174 A | 11/1999 | Bradley et al. | |
| 5,990,092 A | 11/1999 | Walsh | |
| 6,271,198 B1 | 8/2001 | Braisted et al. | |
| 6,440,698 B1 * | 8/2002 | Gurney et al. | ............... 435/69.1 |
| 6,846,805 B2 | 1/2005 | Wolfe | |
| 2003/0119021 A1 | 6/2003 | Koster et al. | |

FOREIGN PATENT DOCUMENTS

| WO | WO 00/26348 A2 | 5/2000 |
|---|---|---|
| WO | WO 03/068168 A3 | 8/2003 |

OTHER PUBLICATIONS

Imanishi, et al., 1996, Supramolecular Science, 3, 13-18.*
Kimberly WT et al., The transmembrane aspartates in presenilin 1 and 2 are obligatory for gamma-secretase activity and amyloid beta-protein generation. *J Biol Chem.* Feb. 4, 2000;275(5):3173-8.
Wolfe et al., Presenilins, APP, and Notch: Proteolysis form womb to tomb. Notch from neurodevelopment to neurodegeneration: Keeping the fate. Springer-Verlag 2002. (Meeting date Mar. 19, 2001, Paris, France).
Bihel J et al. , Discovery of a subnanomolar helical D-tridecapeptide inhibitor of gamma-secretase. J Med Chem. Jul. 29, 2004;47(16):3931-3.
Bird, T.D., Harrison's Principles of Internal Medicine, 14th Ed., Fauci AS et al., eds., New York, McGraw-Hill, 1998, Chapter 26.
Bird T.D., Harrison's Principles of Internal Medicine, 14th Ed., Fauci AS et al., eds., New York, McGraw-Hill, 1998, Chapter 367.
Capobianco A.J., Neoplastic transformation by truncated alleles of human Notch1/Tan1 and Notch2. Mol Cell Biol. Nov. 1997;17(11):6265-73.
Citron M. et al., Mutant presenilins of Alzheimer's disease increase production of 42-residue amyloid beta-protein in both transfected cells and transgenic mice. Nat Med. Jan. 1997;3(1):67-72.
Das C. et al., Designed helical peptides inhibit an intramembrane protease. J Am Chem Soc. Oct. 1, 2003;125(39):11794-5.
De Stropper B. et al., A presenilin-1-dependent gamma-secretase-like protease mediates release of Notch intracellular domain. Nature. Apr. 8, 1999;398(6727):518-22.
Deftos M. L. et al., Notch and presenilins in vertebrates and invertebrates: implications for neuronal development and degeneration. Curr Opin Neurobiol. Feb. 2000;10(1):50-7.
Duff K et al., Increased amyloid-beta42(43) in brains of mice expressing mutant presenilin 1. Nature. Oct. 24, 1996;383(6602):710-3.
Esler W.P. et al., Activity-dependent isolation of the presenilin-gamma -secretase complex reveals nicastrin and a gamma substrate. Proc Natl Acad Sci U S A. Mar. 5, 2002;99(5):2720-5.
Fauci A.S. et al., Harrison's Principles of Internal Medicine, 14th Ed., eds, New York:McGraw-Hill, 1998, Chapter 192.
Fauci A.S. et al., Harrison's Principles of Internal Medicine, 14th Ed., eds, New York:McGraw-Hill, 1998, Chapter 308.
Hardy, J., The Alzheimer family of diseases: many etiologies, one pathogenesis? Proc Natl Acad Sci U S A. Mar. 18, 1997;94(6):2095-7.
Iwatsubo T et al., Visualization of A beta 42(43) and A beta 40 in senile plaques with end-specific A beta monoclonals: evidence that an initially deposited species is A beta 42(43). Neuron. Jul. 1994;13(1):45-53.
Jarrett J.T. et al., The carboxy terminus of the beta amyloid protein is critical for the seeding of amyloid formation: implications for the pathogenesis of Alzheimer's disease. Biochemistry. May 11, 1993;32(18):4693-7.
Jeffries S et al., Neoplastic transformation by Notch requires nuclear localization. Mol Cell Biol. Jun. 2000;20(11):3928-41.
Jiang S et al., Peptide and non-peptide HIV fusion inhibitors.Mol Cell Biol. 2001 Curr. Pharm. Des. 8(8):563-80.
Kang J. et al., The precursor of Alzheimer's disease amyloid A4 protein resembles a cell-surface receptor. Nature. Feb. 19-25, 1987;325(6106):733-6.
Karle I.L. et al. Flexibility in peptide molecules and restraints imposed by hydrogen bonds, the Aib residue, and core inserts. Biopolymers. 1996;40(1):157-80.

(Continued)

*Primary Examiner*—Andrew D Kosar
*Assistant Examiner*—Satyanarayana R Gudibande
(74) *Attorney, Agent, or Firm*—Wolf, Greenfield & Sacks, P.C.

(57) ABSTRACT

Helical peptidomimetic compounds as inhibitors of beta-amyloid production are provided. These inhibitors have sequences with lengths from 11 to 16 amino acids, inclusive. These inhibitors potently inhibit intramembrane proteases, notably aspartyl secretases involved in the enzymatic cleavage of amyloid precursor protein (APP) to yield amyloid-β-peptide. Methods are provided for making a medicament containing the compounds and for administering the compounds to treat β-amyloid-associated diseases, notably Alzheimer's disease.

27 Claims, 3 Drawing Sheets

OTHER PUBLICATIONS

Karle I.L. et al., Structural characteristics of alpha-helical peptide molecules containing Aib residues. Biochemistry. Jul. 24, 1990;29(29):6747-56.

Kornilova A.Y. et al., The initial substrate-binding site of gamma-secretase is located on presenilin near the active site. Proc Natl Acad Sci U S A. Mar. 1, 2005;102(9):3230-5.

Lamb B.T., Presenilins, amyloid-beta and Alzheimer's disease. Nat Med. Jan. 1997;3(1):28-9.

Li Y.M. et al., Photoactivated gamma-secretase inhibitors directed to the active site covalently label presenilin 1. Nature. Jun. 8, 2000;405(6787):689-94.

Lichtenthaler S.F. et al., Mechanism of the cleavage specificity of Alzheimer's disease gamma-secretase identified by phenylalanine-scanning mutagenesis of the transmembrane domain of the amyloid precursor protein. Proc Natl Acad Sci U S A. Mar. 16, 1999;96(6):3053-8.

Milington C.R. et al., Aryl Hydrazides as Linkers for Solid Phase Synthesis which are Cleavable under Mild Oxidative Conditions, Tetrahedron Letters 1998 39:7201-4.

Miranda L.P. et al., Accelerated chemical synthesis of peptides and small proteins. Proc Natl Acad Sci U S A. Feb. 16, 1999;96(4):1181-6.

Moore C.L. et al., Difluoro ketone peptidomimetics suggest a large S1 pocket for Alzheimer's gamma-secretase: implications for inhibitor design. J Med Chem. Sep. 7, 2000;43(18):3434-42.

Roher et al., beta-Amyloid-(1-42) is a major component of cerebrovascular amyloid deposits: implications for the pathology of Alzheimer disease. Proc Natl Acad Sci U S A. Nov. 15, 1993;90(22):10836-40.

Ruchoux M.M. et al., CADASIL: Cerebral autosomal dominant arteriopathy with subcortical infarcts and leukoencephalopathy. J Neuropathol Exp Neurol. Sep. 1997;56(9):947-64.

Scheuner D. et al., Secreted amyloid beta-protein similar to that in the senile plaques of Alzheimer's disease is increased in vivo by the presenilin 1 and 2 and APP mutations linked to familial Alzheimer's disease. Nat Med. Aug. 1996;2(8):864-70.

Schroeter E.H. et al., Notch-1 signalling requires ligand-induced proteolytic release of intracellular domain. Nature. May 28, 1998;393(6683):382-6.

Selkoe D.J., Alzheimer's disease: genotypes, phenotypes, and treatments. Science. Jan. 31, 1997;275(5300):630-1.

Selkoe D.J., Cell biology of the amyloid beta-protein precursor and the mechanism of Alzheimer's disease. Annu Rev Cell Biol. 1994;10:373-403.

Selkoe D.J., Translating cell biology into therapeutic advances in Alzheimer's disease. Nature. Jun. 24, 1999;399(6738 Suppl):A23-31.

Selkoe D.J., Notch and presenilins in vertebrates and invertebrates: implications for neuronal development and degeneration. Curr Opin Neurobiol. Feb. 2000;10(1):50-7.

Thomas N.J. et al., Hereditary vascular dementia linked to notch 3 mutations. CADASIL in British families. Ann N Y Acad Sci. Apr. 2000;903:293-8.

Tomita T. et al., The presenilin 2 mutation (N141I) linked to familial Alzheimer disease (Volga German families) increases the secretion of amyloid beta protein ending at the 42nd (or 43rd) residue. Proc Natl Acad Sci U S A. Mar. 4, 1997;94(5):2025-30.

Wenschuh H. et al., Fmoc Amino Acid Fluorides: Convenient Reagents for the Solid-Phase Assembly of Peptides Incorporating Sterically Hindered Residues. 1994 J Org Chem 59:3275-80.

Wenschuh H. et al., Stepwise Automated Solid Phase Synthesis of Naturally Occurring Peptaibols Using FMOC Amino Acid Fluorides. 1995 J Org Chem 60:405-10.

Wolfe M.S. et al., A substrate-based difluoro ketone selectively inhibits Alzheimer's gamma-secretase activity. J Med Chem. Jan. 1, 1998;41(1):6-9.

Wolfe M.S. et al., Biochemistry. Intramembrane proteases—mixing oil and water. Science. Jun. 21, 2002;296(5576):2156-7.

Wolfe M.S. et al., Intramembrane proteolysis: theme and variations. Science. Aug. 20, 2004;305(5687):1119-23.

Wolfe M.S. et al., Peptidomimetic probes and molecular modeling suggest that Alzheimer's gamma-secretase is an intramembrane-cleaving aspartyl protease. Biochemistry. Apr. 13, 1999;38(15):4720-7.

Wolfe M.S. et al., Two transmembrane aspartates in presenilin-1 required for presenilin endoproteolysis and gamma-secretase activity. Nature. Apr. 8, 1999;398(6727):513-7.

Wolfe M.S. et al., Are presenilins intramembrane-cleaving proteases? Implications for the molecular mechanism of Alzheimer's disease. Biochemistry. Aug. 31, 1999;38(35):11223-30.

Wolfe M.S., Therapeutic strategies for Alzheimer's disease. Nat Rev Drug Discov. Nov. 2002;1(11):859-66.

Zagouras P. et al., Alterations in Notch signaling in neoplastic lesions of the human cervix. Proc Natl Acad Sci U S A. Jul. 3, 1995;92(14):6414-8.

* cited by examiner

HELICAL PEPTIDOMIMETICS WITH ENHANCED ACTIVITY

RELATED APPLICATION

This application claims benefit under 35 U.S.C. 119 (e) of U.S. Provisional Application No. 60/576,965, filed on Jun. 4, 2004, the entire contents of which are incorporated herein by reference.

GOVERNMENT RIGHTS

This invention was funded in part under National Institute of Health Grant No. AG17574. The government may retain certain rights in the invention.

FIELD OF THE INVENTION

The invention relates to compositions and methods for inhibiting intramembrane proteases. More particularly it relates to compounds and methods for inhibiting the enzymatic activity of secretases involved in converting amyloid precursor protein to amyloid-β peptide. The compounds and methods of the invention can be used in the treatment of neurodegenerative disorders, notably Alzheimer's disease, as well as Notch-related diseases.

BACKGROUND OF THE INVENTION

Accumulating biochemical, histological, and genetic evidence supports the hypothesis that the 4 kDa β-amyloid protein (Aβ) is an essential component in the pathogenesis of Alzheimer's disease (AD). Selkoe D J (1997) *Science* 275: 630-631; Hardy J (1997) *Proc Natl Acad Sci USA* 94:2095-2097. Despite the intense interest in the role of Aβ in the etiology of AD, the molecular mechanism of Aβ biosynthesis is poorly understood. The 39-43-residue Aβ is formed via the sequential cleavage of the integral membrane amyloid precursor protein (APP) by β- and γ-secretases. Selkoe D J (1994) *Annu Rev Cell Biol* 10:373-403. β-Secretase cleavage of APP occurs near the membrane, producing the soluble APPs-β and a 12 kDa C-terminal membrane-associated fragment (CTF). The latter is processed by γ-secretase, which cleaves within the transmembrane domain of the substrate to generate Aβ. An alternative proteolytic event carried out by α-secretase occurs within the Aβ portion of APP, releasing APPs-α, and subsequent processing of the resulting membrane-bound 10 kDa CTF by γ-secretase leads to the formation of a 3 kDa N-terminally truncated version of Aβ called p3.

Heterogeneous proteolysis of the 12 kDa CTF by γ-secretase generates primarily two C-terminal variants of Aβ, 40- and 42-amino acid versions ($A\beta_{40}$ and $A\beta_{42}$), and parallel processing of the 10 kDa CTF generates the corresponding C-terminal variants of p3. Although $A\beta_{42}$ represents only about 10% of secreted Aβ, this longer and more hydrophobic variant is disproportionately present in the amyloid plaques observed post mortem in AD patients (Roher A E et al. (1993) *Proc Natl Acad Sci USA* 90:10836-40; Iwatsubo T et al. (1994) *Neuron* 13:45-53), consistent with in vitro studies illustrating the kinetic insolubility of $A\beta_{42}$ vis-à-vis $A\beta_{40}$. Jarrett J T et al. (1993) *Biochemistry* 32:4693-4697. Importantly, all genetic mutations associated with early-onset (<60 years) familial Alzheimer's disease (FAD) result in increased $A\beta_{42}$ production. Selkoe D J (1997) *Science* 275:630-631; Hardy J (1997) *Proc Natl Acad Sci USA* 94:2095-2097. An understanding of the production of Aβ in general and that of $A\beta_{42}$ in particular is helpful for elucidating the molecular mechanism of AD pathogenesis and may also lead to the development of new chemotherapeutic agents which strike at the etiological heart of the disease.

Both γ-secretase and β-secretase are attractive targets for inhibitor design for the purpose of inhibiting production of Aβ. While γ-secretase is an attractive target for inhibitor design, little is known about the structure, mechanism, or binding requirements of this protease. Studies during the past few years suggest that γ-secretase is an unusual aspartyl protease with an intramembrane active site located within a multi-pass membrane protein called presenilin. Wolfe M S (2002) *Nat Rev Drug Discov* 1:859-866; Wolfe M S et al. (2002) *Science* 296:2156-2157; Wolfe M S et al. (2004) *Science* 305:1119-1125.

Helical peptidomimetic inhibitors of intramembrane proteases, notably aspartyl secretases, have been previously reported. Das C (2003) *J Am Chem Soc* 125:11794-11795; U.S. Pat. No. 6,846,805. The helical peptidomimetics included hexa- to decapeptide inhibitors of γ-secretase activity. Interestingly, enantiomers of these compounds, composed exclusively of D-amino acids, were reported to be as potent as their exclusively L-amino acid counterparts.

SUMMARY OF THE INVENTION

It has now been discovered that helical peptidomimetics containing between 11 and 16 amino acids are subnanomolar inhibitors of protease activity. Moreover, the helical peptidomimetics comprised of D-amino acids are equally or more potent than their L-peptide counterparts.

The present invention relates to novel compounds useful for inhibiting certain intramembrane proteases, particularly aspartyl proteases involved in generating β-amyloid from APP, and methods for using same in vivo and in vitro. The compounds are useful, for example, for treating a subject having or at risk of having a β-amyloid-associated disease.

According to a first aspect of the invention, a compound of formula: R1—(R2)$_n$—R3 is provided, wherein R1 is selected from the group consisting of a hydrogen, an acyl, an alkoxycarbonyl, and an aminocarbonyl;

(R2)$_n$ is an oligomer of amino acids R2, each selected independently of any other;

each R2 is independently an achiral, L- or D-amino acid;

n is an integer from 11 to 16, inclusive; and

R3 is selected from the group consisting of a hydroxyl, an alkoxyl, an aryloxyl, an amino, an aminoalkyl, and an aminoaryl; and wherein the compound assumes a substantially helical conformation in solution.

Preferably, (R2)$_n$ includes at least one dipeptide that mimics a secretase cleavage site in an amyloid precursor protein (APP), i.e., the compounds include an (R2)$_n$ containing at least one dipeptide, wherein a secretase which is capable of cleaving APP (e.g., a γ-secretase) is capable of cleaving the dipeptide that mimics the secretase cleavage site in APP. Exemplary dipeptides include Ala-Thr; Val-Ile; Ala-R4, wherein R4 is (1) a hydrophobic amino acid (e.g., glycine, alanine, valine, isoleucine, leucine, phenylalanine, 4-benzoylphenylalanine, tryptophan), (2) a hydrophilic amino acid (e.g., serine, threonine) or (3) a derivatized threonine (e.g., O-benzyl threonine); Val-R5, wherein R5 is a bulky hydrophobic amino acid (e.g., isoleucine, leucine, phenylalanine); and R6-Ile, wherein R6 is a bulky hydrophobic amino acid (e.g., isoleucine, leucine, phenylalanine).

In certain embodiments (R2)$_n$ includes the dipeptide R7-R8, wherein R7 is an alpha, alpha-disubstituted amino acid such as aminoisobutyric acid (Aib), and R8 is a derivatized threonine, such as O-benzyl threonine. In one embodiment R7 is Aib. In one embodiment R8 is O-benzyl threonine.

Preferably, the compounds of the invention assume a helical conformation in solution, e.g., in aqueous solution.

Accordingly, in some embodiments $(R2)_n$ includes at least one helix-inducing amino acid. In some embodiments $(R2)_n$ includes at least two helix-inducing amino acids. Such helix-inducing amino acids can be an alpha, alpha-disubstituted amino acid, including aminoisobutyric acid (Aib). In certain embodiments, at least one R2 is an L-amino acid. In certain embodiments, at least one R2 is a D-amino acid. In these and/or other embodiments, at least one R2 is a hydrophobic amino acid, e.g., glycine, alanine, valine, isoleucine, leucine, phenylalanine, 4-benzoylphenylalanine, tryptophan. Additionally or alternatively, at least one R2 can be a hydrophilic amino acid, e.g., serine, threonine. In particularly preferred embodiments, at least one R2 is an alpha, alpha-disubstituted amino acid, such as Aib.

The compounds of the invention include the following specific embodiments:

to certain of these and/or other embodiments, the β-amyloid-associated disease is Alzheimer's disease. Optionally, the compounds of the invention are administered to the subject in combination with an effective amount of a second agent useful in the treatment of β-amyloid-associated disease, e.g., an acetylcholinesterase inhibitor. In certain preferred embodiments, the compound is orally administered.

In certain embodiments the subject is free of symptoms otherwise calling for treatment with a compound of the invention. In one embodiment the subject is free of symptoms of retrovirus infection. In one embodiment, the subject is free of symptoms of human immunodeficiency virus (HIV) infection.

According to still another aspect of the invention, a method of inhibiting an activity of an intramembrane protease is provided. The method involves contacting an intramembrane

| COMPOUND | SEQ ID NO: |
|---|---|
| Boc-Val-Val-Ile-Aib-Thr(OBz)-Val-Aib-Val-Ile-Aib-OMe | 15 |
| Boc-Aib-Val-Val-Ile-Aib-Thr(OBz)-Val-Aib-Val-Ile-Aib-OMe | 16 |
| Boc-Gly-Aib-Val-Val-Ile-Aib-Thr(OBz)-Val-Aib-Val-Ile-Aib-OMe | 17 |
| Boc-Val-Gly-Aib-Val-Val-Ile-Aib-Thr(OBz)-Val-Aib-Val-Ile-Aib-OMe | 18 |
| Boc-Aib-Val-Gly-Aib-Val-Val-Ile-Aib-Thr(OBz)-Val-Aib-Val-Ile-Aib-OMe | 19 |
| Boc-Leu-Aib-Val-Gly-Aib-Val-Val-Ile-Aib-Thr(OBz)-Val-Aib-Val-Ile-Aib-OMe | 20 |
| Boc-Gly-Leu-Aib-Val-Gly-Aib-Val-Val-Ile-Aib-Thr(OBz)-Val-Aib-Val-Ile-Aib-OMe | 21 | wherein Val is valine; Ile is isoleucine; Thr is threonine; Gly is glycine; Leu is leucine; Boc is t-butyloxycarbonyl; OBz is O-benzyl ester; OMe is O-methyl ester; and Aib is aminoisobutyric acid.

The foregoing embodiments include compounds in which at least one of the recited amino acids is a D-amino acid. Additionally or alternatively, the foregoing embodiments include compounds in which at least one of the recited amino acids is an L-amino acid. In one preferred embodiment all of the recited amino acids are D-amino acids. In another embodiment all of the recited amino acids are L-amino acids.

According to yet another aspect of the invention, pharmaceutical compositions comprising the compounds of the invention and a pharmaceutically acceptable carrier, and methods of making the pharmaceutical compositions by combining a compound of the invention and a pharmaceutically acceptable carrier, are provided. Additionally, pharmaceutically acceptable salts of the compounds of the invention also are provided. Optionally, the pharmaceutical compositions further include a carrier to promote delivery of a compound of the invention to the brain. Thus, the invention embraces the use of the compounds of the invention in the preparation of a medicament for the treatment of a subject having or at risk of having a β-amyloid-associated disease.

According to yet another aspect of the invention, a method of treating a subject having or at risk of having a β-amyloid-associated disease is provided. The method involves administering to a subject having or at risk of having a β-amyloid-associated disease a therapeutically effective amount of a compound of the invention to treat the β-amyloid-associated disease. According to certain embodiments, the β-amyloid-associated disease is a neurodegenerative disease. According protease under conditions in which the intramembrane protease is enzymatically active with an effective amount of a compound of the invention to inhibit the activity of the intramembrane protease. In one embodiment the intramembrane protease is a γ-secretase. In one embodiment the intramembrane protease is a β-secretase. Inhibition of activity can be determined, for example, by observing a decrease in generation of amyloid-β peptide. Such methods can be performed in vivo or in vitro.

The claimed compounds of the invention specifically exclude helical compounds in which helicity is induced through cyclization as described in U.S. Pat. No. 6,271,198, issued to Brainstedt et al. and compounds previously disclosed in Karle I L et al. (1990) *Biochemistry* 29:6747-56; however, the use of such compounds in the preparation of a medicament or in the treatment of a subject having or at risk of having a β-amyloid-associated disease is embraced within the scope of the invention.

According to this aspect of the invention the compound of the invention is as described above, including disclosed embodiments. The compounds of the invention can be packaged in unit dose form for convenience in dosing. In one embodiment the compounds of invention are administered orally.

BRIEF DESCRIPTION OF THE DRAWINGS

The Examples may or may not include figures which are provided for illustrative purposes only and are not required for understanding or practicing the invention.

DETAILED DESCRIPTION

I. Definitions

Figure 1:
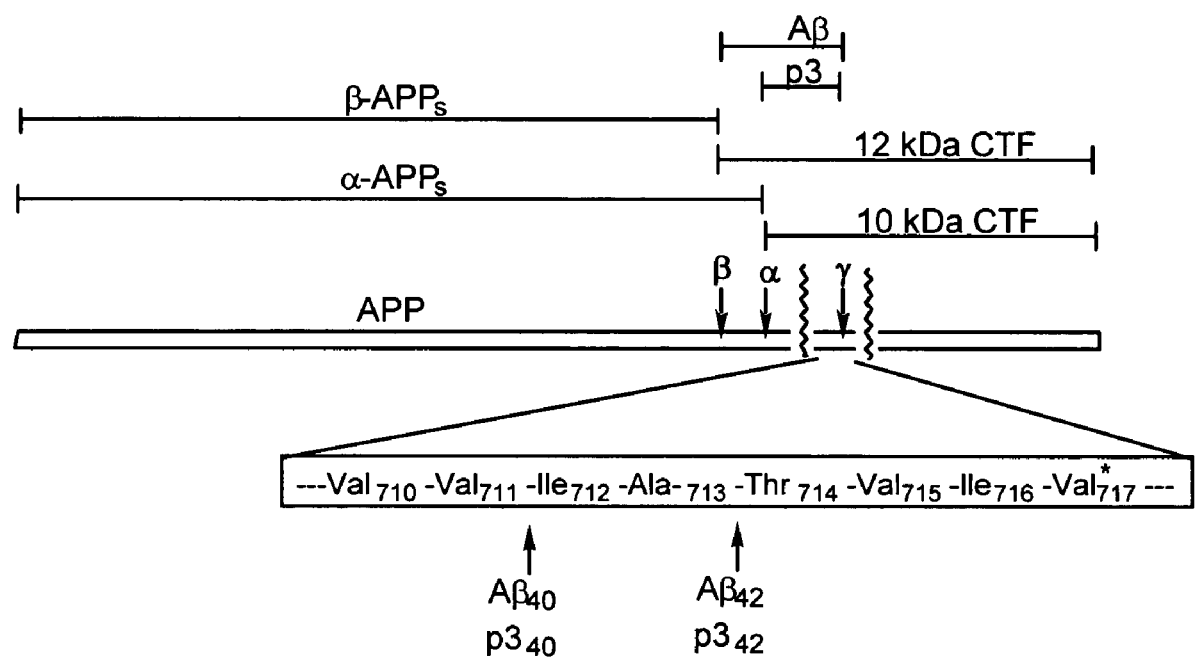
FIG. 1 is a schematic diagram showing various cleavage sites and fragments of APP. Among the fragments are Aβ (including $A\beta_{40}$ and $A\beta_{42}$).

As used herein, chemical terms have their conventional meaning as illustrated by the following illustrative definitions.

Alkyl groups can be linear or branched, saturated or unsaturated, and have up to about ten carbon atoms. One or more hydrogen atoms can also be replaced by a substituent group selected from acyl, amino, carboalkoxy, carboxy, carboxyamido, cyano, halo, hydroxy, nitro, thio, alkyl, cycloalkyl, alkoxy, aryloxy, sulfoxy, and guanido groups. Preferred alkyl groups are "lower alkyl" groups having one to about four carbon atoms. Equally preferred alkyl groups are unsubstituted or include amino, carboxy, carboxyamido, hydroxy, thio and guanido groups. More preferred alkyl groups are methyl, isopropyl, isobutyl, 1-methylpropyl, thiomethylethyl, hydroxymethyl, 1-hydroxyethyl, thiomethyl, carboxyamidomethyl, carboxyamidoethyl, carboxymethyl, carboxyethyl, aminobutyl and guanido.

Cycloalkyl groups have, preferably, saturated or partially unsaturated ring systems, each containing zero to four hetero atoms selected from oxygen, nitrogen and sulfur in a single or fused carbocyclic or heterocyclic ring system having from three to fifteen ring members. Cycloalkyl groups include multicyclic groups having two, three, or more saturated or partially unsaturated rings that can be single, fused, or a combination of single and fused rings. One or more hydrogen atoms can also be replaced by a substituent group selected from acyl, amino, carboalkoxy, carboxy, carboxyamido, cyano, halo, hydroxy, nitro, oxo, thio, alkyl, aryl, cycloalkyl, alkoxy, aryloxy, and guanido groups or two substituents together can form a fused cycloalkyl ring. Examples of a cycloalkyl group include cyclopropyl, cyclobutyl, cyclohexyl, cycloheptyl, morpholinyl, piperidinyl, and pyrrolidinyl. An example of a multicyclic cycloalkyl group is adamantyl. An alkoxy group denotes an oxygen atom substituted with an acyl, alkyl or cycloalkyl group. Examples include methoxy, tert-butyloxy, benzyloxy, and cyclohexyloxy. An aryloxy group denotes an oxygen atom substituted with an aryl group. Examples of aryloxy groups are phenoxy, 4-carbobenzyloxyphenoxy, 4-phenoxyphenoxy. Sulfoxy groups comprise a hexavalent sulfur atom bound to two or three substituents selected from the group consisting of oxo, alkyl, aryl and cycloalkyl groups, wherein at least one of said substituents is oxo.

Aromatic groups can contain a single or fused carbocyclic ring system, having from five to fifteen ring members. One or more hydrogen atoms can also be replaced by a substituent group selected from acyl, amino, carboalkoxy, carboxy, carboxyamido, cyano, halo, hydroxy, nitro, thio, alkyl, aryl, cycloalkyl, alkoxy, aryloxy, sulfoxy, and guanido groups. Arylalkyl groups embrace aryl-substituted alkyl groups. Preferred arylalkyl groups include benzyl, 3-indolylmethyl, 4-hydroxybenzyl, 5-imidazolylmethyl.

Heteroaromatic groups can contain one to four hetero atoms selected from oxygen, nitrogen and sulfur in a single or fused heterocyclic ring system, having from five to fifteen ring members. One or more hydrogen atoms can also be replaced by a substituent group selected from acyl, amino, carboalkoxy, carboxy, carboxyamido, cyano, halo, hydroxy, nitro, thio, alkyl, aryl, cycloalkyl, alkoxy, aryloxy, sulfoxy, and guanido groups. Arylalkyl groups embrace aryl-substituted alkyl groups. Preferred arylalkyl groups include benzyl, 3-indolylmethyl, 4-hydroxybenzyl, 5-imidazolylmethyl.

Peptidyl groups can contain one to ten amino acid residues, amino acid side chains, or amino acid analog residues, usually, but not always, joined in a linear or cyclic fashion by peptide linkages. Amino acid residues can include naturally-occurring and non-naturally-occurring amino acids, examples of which are well known in the art. The following commonly used three-letter symbols are used for amino acids described in the invention: Ala is alanine; Gly is glycine; Ile is isoleucine; Leu is leucine; Phe is phenylalanine; Thr is threonine; Val is valine; etc. In certain embodiments amino acid residues or peptidyl groups can be terminated by O-methyl ester linkages. In certain embodiments adjacent amino acid residues can be joined together by peptide linkages. In certain preferred embodiments, the peptidyl group includes one to four amino acid residues. In certain more preferred embodiments, a peptidyl group includes two amino acid residues. In certain more preferred embodiments, a peptidyl group includes three amino acid residues. In certain more preferred embodiments, a peptidyl group is selected from the group alanine, leucine, phenylalanine, valine, alanine-phenylalanine, leucine-alanine, leucine-leucine, leucine-phenyalanine, leucine-valine, valine-phenylalanine, leucine-valine-alanine, leucine-valine-leucine, leucine-valine-phenylalanine, and leucine-valine-valine.

The pharmaceutically acceptable salts of the compounds of the invention include acid addition salts and base addition salts. The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the invention can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, alginic, β-hydroxybutyric, malonic, and galacturonic acid. Suitable pharmaceutically acceptable base addition salts of compounds of the invention include, but are not limited to, metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine and procaine. All of these salts can be prepared by conventional means from the corresponding compound of the invention by treating, for example, the compound of the invention with the appropriate acid or base.

The compounds of the invention can have centers of asymmetry, i.e., chiral centers. The absolute configuration of these centers can be assigned by the stereochemical descriptors R and S, this R and S notation corresponding to the rules described in *Pure Appl Chem* 45:11-30 (1976). Unless otherwise indicated, the chemical designation of compounds as used herein includes all possible stereochemical isomeric forms.

In certain embodiments individual compounds of the invention include a substantially helical region containing at least two achiral amino acids selected from Aib and other alpha, alpha-disubstituted amino acids, and a plurality of chiral amino acids, as discussed further herein, all of which or substantially all of which are of a single chirality, i.e., all D-amino acids or all L-amino acids. Such individual compounds of the invention of uniform chirality can be used alone or in combination with other individual compounds of the invention of uniform chirality. In particular, a first individual compound of the invention of a uniform chirality can be used in combination with a second individual compound of the invention of uniform but opposite chirality from the first.

The compounds of the invention are thus capable of existing in the form of optical isomers as well as in the form of racemic or non-racemic mixtures thereof. The compounds of the invention can be utilized in the present invention as a single diastereomer or as a mixture of stereochemical isomeric forms. Compounds of the invention typically are synthesized beginning with selected amino acid building blocks of defined chirality. Diastereoisomers can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention can likewise be obtained by utilizing optically active starting materials. These isomers can be in the form of a free acid, a free base, an ester or a salt.

The invention also embraces isolated compounds. An isolated compound refers to a compound which represents at least 10 percent of the compound present in a mixture and exhibits a detectable (i.e., statistically significant) biological activity when tested in conventional biological assays such as those described herein. Preferably the isolated compound represents at least 50 percent of the mixture; more preferably at least 80 percent of the mixture; and most preferably at least 90 percent or at least 95 percent of the mixture.

The invention embraces compounds and methods useful for inhibiting the enzymatic activity of certain intramembrane proteases. An intramembrane protease refers to an enzyme with an active site embedded within a cellular membrane, in which the protease is composed of multiple transmembrane domains. Wolfe M S (1999) *Biochemistry* 38:11223-11230.

As mentioned elsewhere herein, in certain embodiments a subject is free of symptoms of retrovirus infection, including in particular infection by human immunodeficiency virus (HIV). A symptom can be any objectively discernable manifestation of the presence of the retrovirus infection, specifically including laboratory measurement detecting the presence of activity of the virus. Retroviruses are RNA viruses that belong to the family Retroviridae. These viruses characteristically contain an RNA-dependent DNA polymerase (reverse transcriptase) that directs the synthesis of a DNA form of the viral genome after infection of a host cell. The Retroviridae family includes the subfamilies Oncovirinae (oncogenic viruses), for example human T-cell lymphotropic virus (HTLV), Rous sarcoma virus, Abelson leukemia virus, murine mammary tumor virus, and Mason-Pfizer monkey virus; Lentivirinae (slow viruses), which includes HIV-1, HIV-2, Visna virus, and feline immunodeficiency virus; and Spumavirinae (foamy viruses), for example Simian foamy virus and human foamy virus. As their names suggest, many of these viruses cause symptoms related to malignant transformation of infected cells and induction of immunodeficiency that leads to opportunistic infections. Symptoms of infection by specific retroviruses are well known in the art and are described, for example, in *Harrison's Principles of Internal Medicine*, 14$^{th}$ Ed., Fauci A S et al., eds, New York: McGraw-Hill, 1998, Chapters 192 and 308. As used herein, symptoms of HIV infection include both clinical symptoms and levels of viremia associated with any stage of HIV disease, including acute HIV syndrome, asymptomatic stage, early symptomatic disease, neurologic disease, secondary infections, neoplasms, and organ-specific syndromes.

II. Description

According to a first aspect of the invention, a compound of the invention: R1—(R2)$_n$—R3 is provided, wherein R1 is selected from the group consisting of a hydrogen, an acyl, an alkoxycarbonyl, and an aminocarbonyl;

(R2)$_n$ is an oligomer of amino acids R2, each selected independently of any other;

each R2 is independently an achiral, L- or D-amino acid;

n is an integer from 11 to 16, inclusive; and

R3 is selected from the group consisting of a hydroxyl, an alkoxyl, an aryloxyl, an amino, an aminoalkyl, and an aminoaryl.

In one embodiment, (R2)$_n$ includes at least one dipeptide that mimics a secretase cleavage site in an amyloid precursor protein, i.e., the compounds include an (R2)$_n$ containing at least one dipeptide, wherein a secretase which is capable of cleaving APP (e.g., a γ-secretase) is capable of cleaving the dipeptide that mimics the secretase cleavage site in APP.

Exemplary dipeptides include Ala-Thr; Val-Ile; Ala-R4, wherein R4 is (1) a hydrophobic amino acid (e.g., glycine, alanine, valine, isoleucine, leucine, phenylalanine, 4-benzoylphenylalanine, tryptophan), (2) a hydrophilic amino acid (e.g., serine, threonine), or (3) a derivatized threonine (e.g., O-benzyl threonine); Val-R5, wherein R5 is a bulky hydrophobic amino acid (e.g., isoleucine, leucine, phenylalanine); and R6-Ile, wherein R6 is a bulky hydrophobic amino acid (e.g., isoleucine, leucine, phenylalanine).

In one embodiment, the compound assumes a substantially helical conformation in solution. In particular, in one embodiment, the compound assumes a substantially helical conformation in aqueous solution. In yet another embodiment, the compound assumes a substantially helical conformation in a lipid solution. In a certain embodiment the compound assumes a substantially more helical conformation in a lipid environment than in aqeuous environment. Accordingly, in some embodiments $(R2)_n$ includes at least one helix-inducing amino acid. In some embodiments $(R2)_n$ includes at least two helix-inducing amino acids. Such helix-inducing amino acids can be an alpha, alpha-disubstituted amino acid, including aminoisobutyric acid (Aib). In certain embodiments $(R2)_n$ includes Aib-X-X-Aib, wherein X is in each instance any amino acid, including a non-helix-inducing amino acid. A "substantially helical conformation" as used herein denotes at least 25 percent helicity. Percent helicity can be measured using techniques well known in the art, including circular dichroism (CD) and two-dimensional nuclear magnetic resonance (2-D NMR) spectroscopy.

In certain embodiments, at least one R2 is a chiral amino acid. In certain embodiments, at least one R2 is an L-amino acid. In other embodiments, at least one R2 is a D-amino acid. In certain embodiments in which $(R2)_n$ includes more than one chiral amino acid, all chiral amino acids are L-amino acids. In certain other embodiments in which $(R2)_n$ includes more than one chiral amino acid, all chiral amino acids are D-amino acids. The all-D-amino acid-containing embodiments described in Example 1 were equipotent toward inhibiting Aβ production compared to their all-L-amino acid-containing counterparts:

wherein Aib is aminoisobutyric acid; Ala is alanine; Boc is t-butyloxycarbonyl; BPA is 4-benzoylphenylalanine; Gly is glycine; Ile is isoleucine; Leu is leucine; OBz is O-benzyl ester; OMe is O-methyl ester; Thr is threonine; and Val is valine.

Indeed, activity of all-L-form compounds and of all-D-form compounds are additive when used in combination. In contrast, however, it has been found according to the instant invention that activity of a given compound containing a mixture of D- and L-amino acids decreases with loss of uniformity of chirality within the given molecule.

Surprisingly, once the length of the peptides exceeds ten amino acids, the activity of the peptides increases, as shown in Example 2. Even more surprisingly, when the peptide length is 11 to 16 amino acids, inclusive, the all-D-amino acid-containing embodiments described in Example 2 are substantially more potent inhibitors of Aβ production than the corresponding all-L-amino acid-containing counterparts.

In some of these and other embodiments, chiral amino acids are D-amino acids. Embodiments with D-amino acids are believed to be more stable against protease degradation than corresponding embodiments with L-amino acids.

In these and/or other embodiments, at least one R2 is a hydrophobic amino acid, e.g., glycine, alanine, valine, isoleucine, leucine, phenylalanine, 4-benzoylphenylalanine, tryptophan. Additionally or alternatively, R2 can be a hydrophilic amino acid, e.g., serine, threonine. In certain embodiments, at least one R2 is an alpha, alpha-disubstituted amino acid, such as Aib.

In these and/or other embodiments, at least one R2 is a residue that favors helical conformation in peptides. Such residues are readily known to those of ordinary skill in the art. When there is more than one such residue present, they can be arranged in a helix-inducing pattern by repeating every 3 to 4 amino acids. In certain embodiments, such a residue is an alpha, alpha-disubstituted amino acid, such as Aib.

In one embodiment the amino and the carboxyl termini of the compounds of the invention are modified with non-polar

| COMPOUNDS FROM EXAMPLE 1 | SEQ ID NO: |
|---|---|
| Boc-Ala-Thr(OBz)-Aib-Ile-Val-Aib-OMe | 1 |
| Boc-Ile-Ala-Thr(OBz)-Aib-Ile-Val-Aib-OMe | 2 |
| Boc-Aib-Ile-Ala-Thr(OBz)-Aib-Ile-Val-Aib-OMe | 3 |
| Boc-Val-Aib-Ile-Ala-Thr(OBz)-Aib-Ile-Val-Aib-OMe | 4 |
| Boc-Gly-Val-Aib-Ile-Ala-Thr(OBz)-Aib-Ile-Val-Aib-OMe | 5 |
| Boc-Val-Ile-Aib-Thr(OBz)-Val-Aib-OMe | 6 |
| Boc-Val-Val-Ile-Aib-Thr(OBz)-Val-Aib-OMe | 7 |
| Boc-Aib-Val-Val-Ile-Aib-Thr(OBz)-Val-Aib-OMe | 8 |
| Boc-Gly-Aib-Val-Val-Ile-Aib-Thr(OBz)-Val-Aib-OMe | 9 |
| Boc-Val-Gly-Aib-Val-Val-Ile-Aib-Thr(OBz)-Val-Aib-OMe | 10 |
| Boc-D-Val-Gly-Aib-D-Val-D-Val-D-BPA-Aib-D-Thr(OBz)-D-Val-Aib-OMe | 11 | protecting or blocking groups. In a certain embodiment the amino terminus protecting group is t-butyloxycarbonyl. In another embodiment the carboxyl terminus protecting group is methyl ester.

The compounds of the invention include the following specific embodiments:

longer helical peptides such as the D-form of SEQ ID NO:23 (Ac-Val-Gly-Aib-Val-Val-Ile-Aib-Thr(OBz)-Val-Aib-Val-Val-Aib-NH$_2$) not only interact with the initial substrate-binding site but also extend into the active site of γ-secretase. Kornilova A Y et al. (2005) *Proc Natl Acad Sci USA* 102: 3230-3235. While interaction with either site is effective for

| COMPOUNDS OF EXAMPLE 2 | SEQ ID NO: |
|---|---|
| Boc-Val-Val-Ile-Aib-Thr(OBz)-Val-Aib-Val-Ile-Aib-OMe | 15 |
| Boc-Aib-Val-Val-Ile-Aib-Thr(OBz)-Val-Aib-Val-Ile-Aib-OMe | 16 |
| Boc-Gly-Aib-Val-Val-Ile-Aib-Thr(OBz)-Val-Aib-Val-Ile-Aib-OMe | 17 |
| Boc-Val-GLy-Aib-Val-Val-Ile-Aib-Thr(OBz)-Val-Aib-Val-Ile-Aib-OMe | 18 |
| Boc-Aib-Val-Gly-Aib-Val-Val-Ile-Aib-Thr(OBz)-Val-Aib-Val-Ile-Aib-OMe | 19 |
| Boc-Leu-Aib-Val-Gly-Aib-Val-Val-Ile-Aib-Thr(OBz)-Val-Aib-Val-Ile-Aib-OMe | 20 |
| Boc-Gly-Leu-Aib-Val-Gly-Aib-Val-Val-Ile-Aib-Thr(OBz)-Val-Aib-Val-Ile-Aib-OMe | 21 | wherein Aib is aminoisobutyric acid; Boc is t-butyloxycarbonyl; Gly is glycine; Leu is leucine; Ile is isoleucine; OBz is O-benzyl ester; OMe is O-methyl ester; Thr is threonine; and Val is valine.

Thus, the foregoing embodiments include compounds in which at least one of the recited amino acids is a D-amino acid. Additionally or alternatively, the foregoing embodiments include compounds in which at least one of the recited amino acids is an L-amino acid.

The compounds of the invention are useful for inhibiting the enzymatic activity of certain aspartyl proteases in vivo and in vitro. The compounds are particularly potent inhibitors of γ-secretase, the enzyme that catalyzes the final step in the generation of amyloid-β peptide from APP.

γ-Secretase catalyzes the final step in the generation of Aβ from APP and plays a central role in the pathogenesis of Alzheimer's disease. Inhibition of this enzyme by helical peptidomimetics is consistent with inhibition of an intramembranous proteolysis event, the latter being characteristic of γ-secretase.

This aspect of the invention is based, in part, on the discovery that certain helical peptidomimetics (described in the Examples) assume a substantially helical configuration in solution and are capable of inhibiting Aβ production from APP. Although not wishing to be bound to any particular theory or mechanism, it is believed that the compounds of the invention function as peptidomimetics for inhibiting intramembrane proteases in vivo and in vitro. Compounds of this type can be readily synthesized without undue experimentation in a few simple steps from commercially available materials. Significantly, compounds of the invention can inhibit γ-secretase activity in whole cells at sub-nanomolar concentrations. Production of total Aβ and the more fibrillogenic Aβ$_{42}$ is effectively blocked by these compounds, and membrane-associated APP C-terminal fragments (i.e., γ-secretase substrates), are elevated by these compounds in a dose-dependent manner.

Without meaning to be held to any particular theory or mechanism, it is now believed, based on photoaffinity labeling studies, that shorter helical peptides such as the D-form of SEQ ID NO:10, interacts with the initial substrate-binding site, but not the active site, of γ-secretase, whereas slightly inhibiting activity of γ-secretase, it is believed that the ability to interact with both sites may underlie the enhanced inhibitory activity of the compounds of the present invention.

A preferred class of compounds of the invention includes compounds in which R2 contains at least one D-amino acid. Surprisingly, all D-amino acid-containing embodiments described in the Examples were equipotent toward inhibiting Aβ production compared to their L-amino acid counterparts. As noted in the Examples, the therapeutic advantages of using D-amino acid-containing compounds of the invention are significant with respect to, for example, their enhanced metabolic stability.

In certain embodiments the compound of the invention can be a pure R stereoisomer i.e., each and every chiral amino acid or amino acid analog is selected as the R stereoisomer. In alternative embodiments, the compound of the invention can be a pure S stereoisomer, i.e., each and every chiral amino acid or amino acid analog is selected as the S stereoisomer. In yet other alternative embodiments, a compound of the invention can include a mixture of R and S stereoisomers, wherein the ratio of the contribution of one stereoisomer to the other can range from about 1:99 to about 99:1.

Certain embodiments embrace a salt of a compound of the invention. In a preferred embodiment, the salt of the compound is a pharmaceutically acceptable salt as defined above.

According to another aspect of the invention, pharmaceutical compositions containing the compounds of the invention and a pharmaceutically acceptable carrier, as well as methods of making the pharmaceutical compositions by combining a compound of the invention and a pharmaceutically acceptable carrier, are provided. Accordingly, pharmaceutically acceptable salts of the compounds of the invention also are provided. Optionally, the pharmaceutical compositions can further include a carrier to promote delivery of a compound of the invention to the brain.

The pharmaceutically acceptable carrier can be selected on the basis of the desired route of administration of the compound. For example, in one embodiment the carrier is suitable for oral administration. In one embodiment, the composition includes a carrier or additional agent that is suitable for promoting delivery of the compound to the brain. Carriers that can promote delivery of the compound to the brain can include any carrier that promotes translocation across the blood-brain barrier and any carrier that promotes uptake of the compound by neural cells. Examples of such carriers include those disclosed in U.S. Pat. No. 5,604,198 (issued to Poduslo et al.), U.S. Pat. No. 5,827,819 (issued to Yatvin et al.), U.S. Pat. No. 5,919,815 (issued to Bradley et al.), U.S. Pat. No. 5,955,459 (issued to Bradley et al.), and U.S. Pat. No. 5,977,174 (issued to Bradley et al.).

According to yet another aspect of the invention, a method of treating a subject having or at risk of having a β-amyloid-associated disease is provided. The method involves administering to a subject having or at risk of having a β-amyloid-associated disease a therapeutically effective amount of a compound of the invention to treat the β-amyloid-associated disease. A "subject" as used herein refers generally to a mammal, including, in one embodiment, a human. According to certain embodiments, the β-amyloid-associated disease is a neurodegenerative disease. According to certain of these and/or other embodiments, the β-amyloid-associated disease is Alzheimer's disease. Optionally, the compounds of the invention are administered to the subject in combination with an effective amount of a second agent useful in the treatment of β-amyloid-associated disease, e.g., an acetylcholinesterase inhibitor. In certain embodiments, the compound is orally administered.

Thus, the compounds of the present invention are active against a variety of β-amyloid-associated diseases including, for example, Alzheimer's disease and the dementia of Down's syndrome. These neurodegenerative disorders occur in association with, and are believed to be caused by deposition of, amyloid-β peptide in neural tissue, i.e., β-amyloid plaques.

In addition to APP, secretases also have as their substrates members of the Notch family of receptors. De Strooper B et al. (1999) *Nature* 398:518-522. Notch proteins are ligand-activated transmembrane receptors involved in cell-fate selection throughout development. Notch activation results in transcriptional changes in the nucleus through an association with members of the CSL family of DNA-binding proteins (where CSL stands for CBF1, Su(H), Lag-1). It is believed that Notch is cleaved by a protease, enabling the cleaved fragment to enter the nucleus. Signaling by a constitutively active membrane-bound Notch-1 protein requires the proteolytic release of the Notch intracellular domain (NICD), which interacts preferentially with CSL. Schroeter E H et al. (1998) *Nature* 393:382-386.

Although not wishing to be bound to any particular theory or mechanism, it is believed by the applicant that inhibiting γ-secretase also is useful in the treatment of Notch-related diseases, including cerebral autosomal dominant arteriopathy with subcortical infarcts and leukoencephalopathy (CADASIL). A Notch-related disease refers to a disease caused by abnormal Notch-related proteolysis or signaling. For example, a Notch-related disease can arise from a mutation in a Notch receptor causing inappropriate, constitutive Notch activity. Schroeter E H et al. (1998) *Nature* 393:382-386. CADASIL, the most common form of familial vascular dementia, appears to be essentially a disorder of the arteries that is linked to single missense mutations in the Notch 3 gene locus on chromosome 19. Ruchoux M M and Maurage C A (1997) *J Neuropathol Exp Neurol* 56:947-964; Thomas N J et al. (2000) *Ann N Y Acad Sci* 903:293-8. Other Notch-related diseases include certain neoplasms including, for example, acute lymphoblastic T-cell leukemia. Weng A P et al. (2004) *Science* 306: 269-271; Selkoe D J (2000) *Curr Opin Neurobiol* 10:50-7; Deftos M L and Bevan M J (2000) *Curr Opin Immunol* 12:166-72; Jeffries S and Capobianco A J (2000) *Mol Cell Biol* 20:3928-3941; Capobianco A J et al. (1997) *Mol Cell Biol* 17:6265-6273; Zagouras P et al. (1995) *Proc Natl Acad Sci USA* 92:6414-6418.

In view of the foregoing, the compounds of the present invention are also believed to be useful in the treatment of Notch-related diseases, including CADASIL and certain types of neoplasia, e.g., certain leukemias. According to this aspect, the method of treating a subject having or at risk of having a Notch-related disease involves administering to a subject having or at risk of having a Notch-related disease a therapeutically effective amount of a compound of the invention.

Thus, the methods of the invention involve treating a subject afflicted by or susceptible to a disorder that is mediated by a secretase, such as a β-amyloid-associated disease or a Notch-related disease. The method involves administering to a subject having or at risk of having such a disorder, a therapeutically effective amount of a compound of the invention. Preferred subjects of the present invention have a β-amyloid-associated disease. More preferably, subjects of the present invention have Alzheimer's disease and do not have any other β-amyloid-associated disease.

A subject having a β-amyloid-associated disease is a subject with at least one identifiable sign, symptom, or laboratory finding sufficient to make a diagnosis of a β-amyloid-associated disease in accordance with clinical standards known in the art for identifying such disorder. In some instances, the absence of identifiable signs, symptoms, or laboratory findings can be necessary to make a diagnosis. For example, the diagnosis of Alzheimer's disease is most often made as a diagnosis of exclusion based on positive findings in cognitive testing in conjunction with exclusion of other causes. See, for example, Bird T D, In: *Harrison's Principles of Internal Medicine*, 14$^{th}$ Ed., Fauci A S et al., eds, New York: McGraw-Hill, 1998, Chapters 26 and 367. In some instances it can be possible to make a tissue diagnosis.

A subject at risk of having a β-amyloid-associated disease is a subject with an identifiable risk factor for developing a β-amyloid-associated disease. For example, a subject at risk of having a β-amyloid-associated disease can include a member in a family with familial Alzheimer's disease. Another example of a subject at risk of having a β-amyloid-associated disease is a subject over the age of 40 with Down's syndrome.

According to this aspect of the invention, the novel compositions disclosed herein are placed in a pharmaceutically acceptable carrier and are delivered to a recipient subject (preferably a human) in accordance with known methods of drug delivery. The compounds of the present invention can be administered alone or in combination with at least one other agent known or believed to be useful for treating a β-amyloid-associated disease. In general, the methods of the invention for delivering the compositions of the invention in vivo utilize art-recognized protocols for delivering the agent with the only substantial procedural modification being the substitution of the compounds of the invention for the drugs in the art-recognized protocols.

Other agents which are known or believed to be useful in the treatment of a β-amyloid-associated disease include acetylcholinesterase inhibitors, particularly tetrahydroaminoacridine (tacrine hydrochloride, COGNEX® (Parke-Davis)), donepezil (ARICEPT®, Pfizer), rivastigmine (EXELON®, Novartis), and galantamine (REMINYL®, Janssen).

The phrase "therapeutically effective amount" means that amount of a compound which prevents the onset of, alleviates the symptoms of, or stops the progression of a disorder or disease being treated. The phrase "therapeutically effective amount" means, with respect to a β-amyloid-associated disease, that amount of a compound of the invention which prevents the onset of, alleviates the symptoms of, or stops the progression of a β-amyloid-related disorder or disease. In general such symptoms are, at least in part, the result of the accumulation of increased amounts of amyloid-β peptide in vivo. Thus, a "β-amyloid-associated disease" is a condition that is characterized by certain clinical features and which, it is generally believed, is associated with excessive amounts of amyloid-β peptide. "Excessive," with respect to amounts of amyloid-β peptide, refers to an amount of amyloid-β peptide which is (1) greater than the amount of amyloid-β peptide that occurs in a normal, healthy subject, and (2) results in an adverse medical condition. The term "treating" is defined as administering, to a subject, a therapeutically effective amount of a compound of the invention (e.g., SEQ ID NO:18) that is sufficient to prevent the onset of, alleviate the symptoms of, or stop the progression of a disorder or disease being treated.

The pharmaceutical preparations disclosed herein are prepared in accordance with standard procedures and are administered at dosages that are selected to reduce, prevent, or eliminate, or to slow or halt the progression of, the condition being treated (See, e.g., *Remington's Pharmaceutical Sciences*, Mack Publishing Company, Easton, Pa., and *Goodman and Gilman's The Pharmaceutical Basis of Therapeutics*, Pergamon Press, New York, N.Y., the contents of which are incorporated herein by reference, for a general description of the methods for administering various agents for human therapy). In one embodiment the compositions of the invention can be delivered using controlled or sustained-release delivery systems (e.g., capsules, bioerodable matrices). Exemplary delayed-release delivery systems for drug delivery that would be suitable for administration of the compositions of the invention are described in U.S. Pat. Nos. U.S. Pat. No. 5,990,092 (issued to Walsh); U.S. Pat. No. 5,039,660 (issued to Leonard); U.S. Pat. No. 4,452,775 (issued to Kent); and U.S. Pat. No. 3,854,480 (issued to Zaffaroni).

The pharmaceutically acceptable compositions of the present invention include one or more compounds of the invention in association with one or more nontoxic, pharmaceutically acceptable carriers and/or diluents and/or adjuvants and/or excipients, collectively referred to herein as "carrier" materials, and if desired, other active ingredients.

The compounds of the present invention can be administered by any route, preferably in the form of a pharmaceutical composition adapted to such a route, and would be dependent on the condition being treated. The compounds and compositions can, for example, be administered orally, intravascularly, intramuscularly, subcutaneously, intraperitoneally, or topically. The preferred method of administration is oral administration. In one embodiment the method of administration involves direct administration to brain.

For oral administration, the pharmaceutical compositions can be in the form of, for example, a tablet, capsule, suspension or liquid. The pharmaceutical composition is preferably made in the form of a dosage unit containing a therapeutically effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs can contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The pharmaceutical compositions can also be administered parenterally via injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient. Suitable carriers for topical administration include oil-in-water or water-in-oil emulsions using mineral oils, petrolatum and the like, as well as gels such as hydrogel. Alternative topical formulations include shampoo preparations, oral pastes and mouthwash.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution at the time of delivery.

The dosage regimen for treating a β-amyloid-associated disease with the compound and/or compositions of this invention is selected in accordance with a variety of factors, including the type, age, weight, sex and medical condition of the patient, the severity of the β-amyloid-associated disease, the route and frequency of administration, and the particular compound employed. In general, dosages are determined in accordance with standard practice for optimizing the correct dosage for treating a β-amyloid-associated disease.

The dosage regimen can be determined, for example, by following the response to the treatment in terms of cognitive studies. Examples of such cognitive studies are well known in the art, and they include the mini-mental status examination. See, for example, Bird T D, *In: Harrison's Principles of Internal Medicine*, 14$^{th}$ Ed., Fauci A S et al., eds, New York: McGraw-Hill, 1998, Chapter 26. In addition, because the compounds of the invention are believed to inhibit the synthesis of β-amyloid in vivo, the dosage regimen can also be determined by measurement of β-amyloid. It should be noted that β-amyloid is released into the blood and the cerebrospinal fluid (CSF), and is not confined to neural tissue. Therefore, the dosage regimen can also be determined by correlating serial measurement of β-amyloid present in blood or in CSF to the dose of the compositions of this invention. Methods of measuring β-amyloid present in blood or in CSF can include, for example, methods based on Aβ-specific ELISA.

The compositions can contain from 0.01% to 99% by weight of the active ingredient, depending on the method of administration.

In a further aspect of the invention, a method is provided for inhibiting activity of an intramembrane protease. The method involves contacting a compound of the invention with an intramembrane protease under conditions in which the intramembrane protease is enzymatically active upon its substrate when the compound is not present, in an amount effective to result in a detectable inhibition of the activity of the intramembrane protease. Also included in this method is contacting an intramembrane protease with a combination of two or more compounds of the invention to inhibit the intramembrane protease. In a preferred embodiment of this aspect of the invention, the intramembrane protease is γ-secretase. The compounds of the invention can be used alone or in combination with other compounds that inhibit aspartyl protease activity. In certain embodiments a compound of the invention is contacted with an intramembrane protease in vitro. The intramembrane protease can be isolated or cellular for in vitro assays. In certain other embodiments a compound of the invention is contacted with an intramembrane protease in vivo.

The inhibitory effect of a compound of unknown inhibitory activity can be assessed, for example, by monitoring intramembrane protease activity according to standard techniques. For example, a γ-secretase enzyme is maintained under conditions suitable for β-amyloid formation, the enzyme is contacted with the compound to be tested, and formation of the β-amyloid is monitored by standard assay, such as by ELISA. More specifically for γ-secretase, since reduced γ-secretase activity leads to an increase in γ-secretase substrate, a γ-secretase enzyme is maintained under conditions suitable for β-amyloid formation, the enzyme is contacted with the compound to be tested, and accumulation or concentration of the γ-secretase substrate is monitored by standard assay, such as by Western blotting. A reduction in the enzyme activity measured in the presence of the compound, as compared with the activity in the absence of compound, is indicative of inhibition of γ-secretase activity by the compound. In an effort to ensure the integrity of the assay, a parallel assay can be conducted in which the inhibitory activity of a compound of the invention with known inhibitory activity is assessed. Since the compounds of the invention are now shown to be inhibitors of γ-secretase, they can serve as positive controls for the assay of compounds of unknown inhibitory activity. The absence of inhibition in an assay using a compound of the invention is indicative of a problem in the assay itself.

EXAMPLES

The following examples are illustrative only and are not intended to limit the scope of the invention in any way.

Considerable evidence now supports the amyloid hypothesis of Alzheimer's disease (AD), which holds that aggregation of the β-amyloid protein (Aβ) is the primary molecular insult initiating a cascade of events that ultimately lead to neurodegeneration and dementia. Aβ is spliced out of a larger protein called the amyloid-β precursor protein (APP), and the last step in Aβ formation is cleavage by γ-secretase, an enzyme considered an important therapeutic target for AD. The inhibitors of γ-secretase disclosed in (22) and Patent Appl. Pub. No. US 2003/0186877, and herein were developed as molecular probes to help characterize this protein-cleaving enzyme, or protease. These inhibitor studies, along with computer modeling, molecular biology, and biochemical purification, suggest that γ-secretase is a very unusual protease that cleaves within a lipid environment inside cells. The novel compounds of the invention take advantage of this unique property of the protease. In a lipid environment, proteins typically assume a spiral or helical shape, and this should also be true for the part of APP that is cleaved by γ-secretase. It was discovered that small peptides can take on a similar helical shape and mimic APP and that these compounds inhibit γ-secretase and block Aβ production. Importantly, it was also found that compounds that are made up of D-amino acids have the same potency as compounds made of L-amino acids. Because D-amino acid containing peptides are typically very stable in the body, these compounds represent new leads for drug development.

Postmortem analysis of AD brains reveals numerous amyloid plaques, proteinaceous clumps associated with dead and dying neurons (1). The primary protein component of these plaques is the amyloid-β protein (Aβ), a 4 kDa protein derived from a larger membrane protein of unknown function called the amyloid-β precursor protein (APP) (2). Aβ is formed from the type I integral membrane protein APP through two protease activities (3). First, β-secretase cleaves APP at the Aβ N-terminus, resulting in a soluble form of APP (α-APP$_2$) and a 99-residue 12 kDa C-terminal fragment (C99; see FIG. 1). This C-terminal fragment is then further processed by γ-secretase to Aβ through an unusual cleavage that occurs within the single transmembrane region. In addition, γ-secretase cleaves APP within the Aβ formation. This α-secretase cleavage likewise leads to release of a soluble form of APP (α-APPs) and an 83-residue 10 kDa C-terminal fragment (C83). C83 also serves as a substrate for γ-secretase to form a 3 kDa protein (p3) that represents an N-terminally truncated Aβ.

The two primary forms of Aβ are the 40- and 42-amino acid C-terminal variants, Aβ$_{40}$ and Aβ$_{42}$. The longer and more hydrophobic Aβ$_{42}$ is particularly implicated in amyloid plaque formation and in the pathogenesis of AD (4-6). Importantly, genetic mutations linked to familial early-onset (<60 years) autosomal dominant AD (FAD) all result in increased Aβ$_2$ production (4-6). Such FAD-causing mutations include those in the APP gene itself, and these mutations lie near the β- and γ-secretase cleavage sites. Mutations in APP, however, account for only a small fraction of FAD cases. Most are caused by mutations in two integral membrane proteins called presenilins 1 and 2 (4-6). These presenilin mutations lead to specific increases in Aβ$_{42}$ formation in transfected cell lines (7, 8) and in transgenic mice (7, 9). Also, subjects with FAD-linked presenilin 1 (PS1), presenilin 2 (PS2), or APP mutations have elevated plasma Aβ$_{42}$ and increased Aβ$_{42}$ in media from primary fibroblast cultures (10). The discovery that mutations in the presenilin genes account for the majority of FAD cases has generated a flurry of activity to determine the normal biological roles of the corresponding proteins and how these proteins influence Aβ$_{42}$ production.

The identity of γ-secretase has remained elusive, despite the importance of this enzyme to AD etiology and treatment. Small, substrate-based transition-state analogue inhibitors of γ-secretase were developed, and these compounds have served as useful probes for understanding this mysterious protease (11-13). The inhibitor studies support an aspartyl protease mechanism for γ-secretase (12). Moreover, molecular modeling (12) and mutagenesis experiments (14) suggest a helical model for the APP transmembrane region upon initial binding to γ-secretase. This is consistent with the hypothesis that this enzyme catalyzes an unusual intramembranous proteolysis. It was also found that two transmembrane aspartates in presenilins are critical for γ-secretase activity, suggesting that presenilins themselves are γ-secretases, novel aspartyl proteases containing an intramembranous active site (15). In support of this, it has been reported that presenilins are the molecular target for aspartyl protease transition-state analogue γ-secretase inhibitors (16, 17), strong evidence that the active site of the protease resides in presenilin. More recently, an immobilized transition-state analogue inhibitor was used to show that presenilins and nicastrin (a presenilin-associated protein), track closely with γ-secretase activity (18). Moreover, it was found that C83, a γ-secretase substrate, quantitatively copurifies with presenilin and nicastrin from this affinity matrix (18), whereas very little full-length APP binds to the matrix. Although not wishing to be bound to any particular theory or mechanism, this finding provides evidence for a separate initial substrate binding site, since the active site is occupied by the inhibitor during this purification step. After docking into this initial site, the substrate can then access the active site via conformational change.

Modeling (12) and mutagenesis (14) suggest a helical conformation for the transmembrane region of the substrate upon initial interaction with γ-secretase. Indeed, it was found that helical peptides based on the APP γ-secretase cleavage site block this protease activity in cell culture. Importantly, helical D-peptides were also found to block γ-secretase activity with equal potency to their L-peptide counterparts, representing new therapeutic agents, as well as new leads for drug development.

Example 1

Shorter Peptidomimetics

Based on the helical model for the APP transmembrane domain, short peptides were designed to adopt a similar conformation that block γ-secretase activity. Judicious replacement of selected residues of short APP-derived peptides with 2-aminoisobutyric acid (Aib), a known helix-inducing amino acid (19, 20), provided peptides that, in principle, mimic the γ-secretase cleavage site on one face of the helix, with Aib residues on the other face. Aib-containing peptides were identified that inhibit Aβ production in APP-transfected cells with 50 percent inhibitory concentrations ($IC_{50}$'s) as low as 2 μM. This inhibition occurs at the γ-secretase level: γ-secretase substrates C99 and C83 were substantially increased in the presence of Aib-containing peptides. The inhibitory activity of the compounds was specific for γ-secretase; the compounds did not affect β-secretase activity. Conformational studies by circular dichroism (CD) showed that these peptides indeed display helical character in solution. It was also discovered that an Aib decapeptide that is not based on the APP sequence (VIIb in ref. 19): Boc-Aib-Ala-Leu-Aib-Ala-Leu-Aib-Ala-Leu-Aib-OMe (SEQ ID NO:13) also blocked Aβ production with an $IC_{50}$ of 2 μM. The crystal structure of this compound has been determined, and the peptide is fully helical (19). In certain embodiments the compounds of the invention have structures that are based on the partial APP sequence Val-Gly-Gly-Val-Val-Ile-Ala-Thr-Val-Ile-Val-Ile (SEQ ID NO:12; see FIG. 1). Basing the structures of the compounds of the invention on the partial APP sequence could enhance in vivo specificity of the compounds. As an added benefit, it was also found that these highly hydrophobic peptides are reasonably soluble, whereas their non-Aib counterparts are insoluble even in DMSO.

Surprisingly, all-D-amino acid containing peptide counterparts were equipotent toward inhibiting Aβ production. These peptides likewise assumed a helical conformation, although of the opposite sense (left-handed instead of right-handed). Thus, the invention advantageously provides helical peptidomimetics having improved metabolic stability.

TABLE 1

Sequence of the γ-secretase cleavage site within the APP transmembrane region and designed peptidomimetic inhibitors (asterisks in APP denote sites of cleavage resulting in $Aβ_{40}$ and $Aβ_{42}$ production):

| SEQ ID NO: | Peptide | $IC_{50}$ (μM) |
|---|---|---|
| 12 | APP Transmembrane Region:<br>Val-Gly-Gly-Val-Val*Ile-Ala*Thr-Val-Ile-Val-Ile | |
| 1 | Designed Peptidomimetics:<br>Boc-Ala*Thr(OBz)-Aib-Ile-Val-Aib-OMe | 25 |
| 2 | Boc-Ile-Ala*thr(OBz)-Aib-Ile-Val-Aib-OMe | 15 |
| 3 | Boc-Aib-Ile-Ala*Thr(OBz)-Aib-Ile-Val-Aib-OMe | 10 |
| 4 | Boc-Val-Aib-Ile-Ala*Thr(OBz)-Aib-Ile-Val-Aib-OMe | 2 |
| 5 | Boc-Gly-Val-Aib-Ile-Ala*Thr(OBz)-Aib-Ile-Val-Aib-OMe | 5 |
| 6 | Boc-Val*Ile-Aib-Thr(OBz)-Val-Aib-OMe | 12 |
| 7 | Boc-Val-Val*Ile-Aib-Thr(OBz)-Val-Aib-OMe | 6 |
| 8 | Boc-Aib-Val-Val*Ile-Aib-Thr(OBz)-Val-Aib-OMe | 6 |
| 9 | Boc-Gly-Aib-Val-Val*Ile-Aib-Thr(OBz)-Val-Aib-OMe | 3 |
| 10 | Boc-Val-Gly-Aib-Val-Val*Ile-Aib-Thr(OBz)-Val-Aib-OMe | 3 |

The top set of peptidomimetics (SEQ ID NOs: 1-5) was designed considering the cleavage leading to A$\beta_{42}$, and the bottom set (SEQ ID NOs: 6-10) was designed considering the cleavage site leading to A$\beta_{40}$. IC$_{50}$ is the concentration of compound that reduced production of total A$\beta$ by 50% in a cell-based assay using Chinese hamster ovary (CHO) cells stably transfected with human APP. All-D-peptide versions of compounds 6-10 showed low micromolar activity, similar to the all-L-peptides.

In addition to the foregoing helical peptidomimetics, the following helical peptidomimetic was found to have an IC$_{50}$ of 100 nM (0.1 µM) in the same cell-based assay using CHO cells stably transfected with human APP: Boc-D-Val-Gly-Aib-D-Val-D-Val-D-BPA-Aib-D-Thr(OBz)-D-Val-Aib-OMe (SEQ ID NO:11).

Example 2

Parallel Synthesis Stucture-Activity Study

Parallel synthesis of related peptides is used to further define structure-activity relationships at each position and optimize potency of these compounds.

To more rapidly identify potent peptides of this type, parallel solid-phase peptide synthesis is employed using an Argonaut Quest 210 semi-automated apparatus. Each position of the D-peptide version of decapeptide SEQ ID NO:10 is systematically varied. A variety of hydrophobic D-amino acids (Ala, Val, Ile, Leu, Phe, Thr(OBz), Tyr, Trp, Gly, Asn, Gln) is installed into the non-Aib positions. Hydrophobic residues are chosen because of the general preference of $\gamma$-secretase for this characteristic. $\alpha$-Methyl amino acids of D-Val, D-Leu, and D-Phe were also installed into each position. These commercially available alpha, alpha-disubstituted amino acids, such as Aib, should increase the helicity of the peptides and add steric bulk to fill large hydrophobic pockets in $\gamma$-secretase (13, 14).

While alpha, alpha-dialkylated amino acids such as Aib cause difficulties for solid-phase peptide synthesis (SPPS) due to steric hindrance of coupling, the use of 9-Fluorenylmethoxycarbonyl (Fmoc) amino acid fluorides makes possible the facile, general assembly of such peptides (21). Thus, by this means peptide analogs containing multiple Aibs (even one with four contiguous Aibs) are obtained in good yield and high purity. Standard o-chlorotrityl resin is loaded with a D-amino alcohol, and the loading is determined by UV analysis. The loaded resin is deprotected with 20% piperidine in dimethylformamide (DMF), and coupled to Fmoc-Aib-F. The resin-bound dipeptide is then deprotected and sequentially coupled to Fmoc-amino acid fluorides. The resin is split before final coupling to the various amino acid residues, providing compounds that allowed optimization of the first position. These compounds are N-capped with acetyl and cleaved from the resin. Validation of this synthetic method is performed through synthesis of a single sterically congested peptide (Ac-Ile-Ile-Aib-Ile-Ile-Aib-Ile-ol, SEQ ID NO:14). This method has successfully provided a variety of peptaibols, bioactive 20-mer peptides with up to 10 Aibs, in high yield and purity and without significant racemization (21).

The 15 D-peptides, varied in first position, are tested for their ability to inhibit total A$\beta$ production in APP-transfected cell lines using a sensitive, quantitative, and convenient sandwich ELISA as previously described (12, 13). The compound best able to reduce A$\beta$ production is then used as a starting point for the synthesis of a second round of peptide synthesis, 15 compounds each defined at the second position and containing the optimal first residue. In this iterative fashion, the optimal residue for each position is determined. Final purification of all compounds is performed by preparative high pressure liquid chromatography (HPLC), and characterization is performed by amino acid analysis and mass spectrometry. The effects of the most potent peptides on other APP proteolytic fragments (C99, C83, $\alpha$- and $\beta$-APPs) are examined as before (11, 13) to determine the extent to which these compounds block A$\beta$ production at the $\gamma$-secretase level.

Example 3

Longer Peptidomimetics

Herein a new series of extended helical L- and D-peptides is disclosed, containing between 10 and 16 amino acids and designed from the APP transmembrane domain, in order to evaluate the relationship between peptide length and inhibitory activity. It was reasoned that longer peptides might be more effective due to increased helical character and a larger surface area for interaction with the protease. One of these compounds displayed remarkably high potency, with an IC$_{50}$ of 140 pM.

Figure 2:
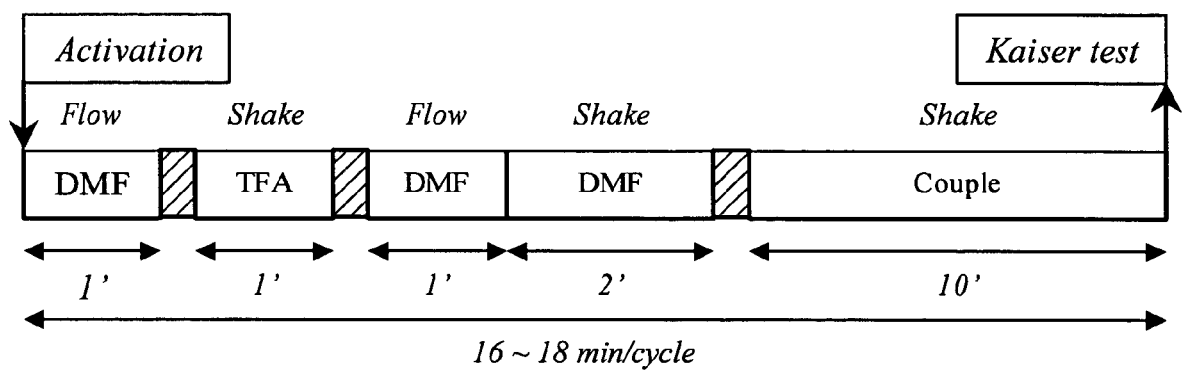
FIG. 2 is a schematic diagram showing manual solid phase synthesis. The hatched regions indicate a drainage step where excess solvent and/or reactant components are removed from the peptide-resin by filtration. TFA, trifluoroacetic acid; DMF, dimethylformamide.
Figure 3:
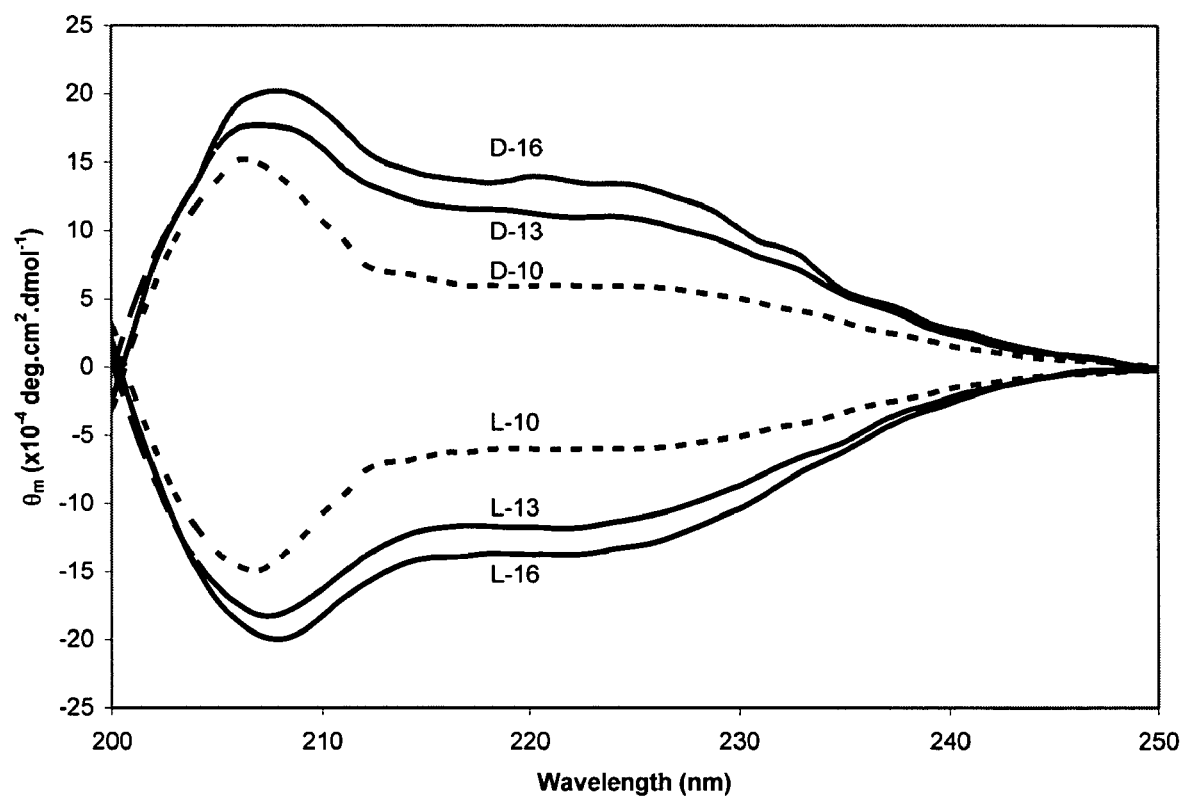
FIG. 3 is a graph depicting a circular dichroism (CD) spectra of D- and L-peptide enantiomeric pairs containing 10, 13 and 16 amino acids. Troughs at 206-208 nm and at 220-223 nm are characteristic of a right-handed helix, while peaks at these wavelengths are characteristic of a left-handed helix. The molar ellipticity per amino acid increases with the peptide length. L-10 and D-10, L- and D-forms, respectively, of SEQ ID NO:15; L-13 and D-13, L- and D-forms, respectively, of SEQ ID NO:18; L-16 and D-16, L- and D-forms, respectively, of SEQ ID NO:21.

The peptides in Example 1 contained N-Boc and O-methyl ester termini and were synthesized following a standard liquid-phase procedure with N,N,N',N'-Tetramethyl-O-(7-azabenzotriazol-1-yl)uronium hexafluorophosphate (HATU) as the coupling reagent in presence of diisopropylethylamine (DIEA) in DMF (22). This synthetic strategy was suitable for peptides containing up to 10 amino acids; however, the extension of the peptide chain beyond 10 residues became difficult, particularly during the intermediate purification steps. In spite of their potential helicity, the hydrophobic character of these peptides apparently did not favor solubility in common solvents such as dichloromethane or ethyl acetate, leading to a time-consuming synthesis and a dramatic drop-off in yields. To solve this problem, solid-phase peptide synthesis (SPPS) using Boc-amino acids was utilized. This strategy had the advantage of clean, reliable, and rapid acidolytic N$^{\alpha}$-Boc deprotection compared with its Fmoc counterpart (23, 24). SPPS was performed using a hydrazinobenzoyl resin, which is stable to acids and bases and can be cleaved with high specificity under mild oxidative conditions (25). HATU was selected instead of other activators such as 2-(1H-benzotriazole-1-yl)-1,1,3,3-tetramethyluronium hexafluorophosphate (HBTU) or benzotriazole-1-yl-oxy-tris-pyrrolidino-phosphonium hexafluorophosphate (PyBOP) because it leads to superior acylation rates, reduces racemization, and has higher solubility in the common coupling solvent DMF (22). Each cycle of deprotection, draining, washing, and coupling was optimized to be complete in less than 20 minutes (FIG. 2). After chain assembly, cleavage from the solid-phase was accomplished by treating with copper(II) acetate in a mixture pyridine/methanol. After purification by preparative HPLC, the identity and purity of the final compounds were verified by mass spectroscopy and analytical HPLC, respectively. The helical conformation of this peptide family was demonstrated by circular dichroism (CD) and 2D NMR (22). According to the CD data, the helical character increased with the length of the peptide as predicted (FIG. 3).

Compounds were tested in a $\gamma$-secretase assay using detergent-solubilized membranes from HeLa cells and a recombinant APP-based substrate (Table 2, 18). In the L-series, compound with SEQ ID NO:17 was the most potent, with an IC$_{50}$ of 360 nM, a~100-fold increase in potency over the reference L-decapeptide having SEQ ID NO:10 (IC$_{50}$=30 µM). Moreover, the $\gamma$-secretase inhibition appears to show dependence on length. Extending the peptide up to 12 amino acids enhanced $\gamma$-secretase inhibition, but further extensions resulted in stepwise decreases in inhibitory activity. Extension of the C-terminus of reference L-decapeptide having SEQ ID NO:10 with Val-Ile-Aib improved potency, as the resultant peptide with SEQ ID NO:18 was almost 40 times more active, with an IC$_{50}$ of 780 nM.

Unexpectedly, the D-series was much more potent than the L-series. Starting from the reference D-decapeptide having SEQ ID NO:10 ($IC_{50}$=90 nM), the enantiomers of the helical peptide L-series were tested for inhibitory activity. These D-peptides all showed very potent activity, with $IC_{50}$ values generally in the 10-30 nM range. Surprisingly, the activity did not change much with the length of the peptide in most cases. However, the compound with SEQ ID NO:18 was extremely potent, with an $IC_{50}$ of 140 pM, 100 times more active than the other analogs of the D-series. The compound with SEQ ID NO:18 was also tested in a cell-based assay from APP-transfected CHO cells (12), in which it showed an $IC_{50}$ of 9±1 nM. This greater than 40-fold loss of activity compared to the cell-free assay may be due to the need to enter into and/or cross cell membranes or some susceptibility to metabolic degradation.

best γ-secretase inhibitors yet reported and represents a potential drug lead. Indeed, the helical conformation along with the D-configuration should increase the metabolic stability of these peptides, which is highly valuable from the perspective of drug development.

References

1. Selkoe, D. J. (1999) *Nature* 399:A23-31.
2. Kang, J., et al. (1987) *Nature* 325:733-6.
3. Selkoe, D. J. (1995) *Annu Rev Cell Biol* 10:373-403.
4. Hardy, J. (1997) *Proc Natl Acad Sci USA* 94:2095-7.
5. Selkoe, D. J. (1997) *Science* 275:630-1.
6. Lamb, B. T. (1997) *Nat Med* 3:28-8.
7. Citron, M., et al. (1997) *Nat Med* 3:67-72.
8. Tomita, T., et al. (1997) *Proc Natl Acad Sci USA* 94:2025-30.

TABLE 2

Aib-containing peptides and their inhibitory potency toward γ-secretase.

| SEQ ID NO: | Peptide | Cell-free Assay $IC_{50}$ (nM) [d] |
|---|---|---|
| | APP transmembrane residues 704-720 [a] | |
| 22 | Gly-Leu-Met-Val-Gly-Gly-Val-Val*-Ile-Ala*-Thr-Val-Ile-Val-Ile-Thr | |
| | L-peptides [b] | |
| 10 | Boc-Val-Gly-Aib-Val-Val-Ile-Aib-Thr(OBz)-Val-Aib-OMe | 30,000 [e] |
| 15 | Boc-Val-Val-Ile-Aib-Thr(OBz)-Val-Aib-Val-Ile-Aib-OMe | 10,000 ± 1,000 |
| 16 | Boc-Aib-Val-Val-Ile-Aib-Thr(OBz)-VaI-Aib-Val-Ile-Aib-OMe | 3,100 ± 500 |
| 17 | Boc-Gly-Aib-Val-VaI-Ile-Aib-Thr(OBz)-Val-Aib-Val-Ile-Aib-OMe | 360 ± 30 |
| 18 | Boc-Val-Gly-Aib-Val-Val-Ile-Aib-Thr(OBz)-Val-Aib-Val-Ile-Aib-OMe | 780 ± 140 |
| 19 | Boc-Aib-Val-Gly-Aib-Val-Val-Ile-Aib-Thr(OBz)-Val-Aib-Val-Ile-Aib-OMe | 910 ± 170 |
| 20 | Boc-Leu-Aib-Val-Gly-Aib-Val-Val-Ile-Aib-Thr(OBz)-Val-Aib-Val-Ile-Aib-OMe | 4,700 ± 500 |
| 21 | Boc-Gly-Leu-Aib-Val-Gly-Aib-Val-Val-Ile-Aib-Thr(OBz)-Val-Aib-Val-Ile-Aib-OMe | 11,000 ± 3,500 |
| | D-peptides [c] | |
| 10 | Boc-Val-Gly-Aib-Val-Val-Ile-Aib-Thr(OBz)-Val-Aib-OMe | 90 [e] |
| 15 | Boc-Val-Val-Ile-Aib-Thr(OBz)-Val-Aib-Val-Ile-Aib-OMe | 25 ± 3 |
| 16 | Boc-Aib-Val-Val-Ile-Aib-Thr(OBz)-Val-Aib-Val-Ile-Aib-OMe | 28 ± 19 |
| 17 | Boc-Gly-Aib-Val-Val-Ile-Aib-Thr(OBz)-Val-Aib-Val-Ile-Aib-OMe | 12 ± 4 |
| 18 | Boc-Val-Gly-Aib-Val-Val-Ile-Aib-Thr(OBz)-Val-Aib-Val-Ile-Aib-OMe | 0.14 ± 0.07 |
| 19 | Boc-Aib-Val-Gly-Aib-Val-Val-Ile-Aib-Thr(OBz)-Val-Aib-Val-Ile-Aib-OMe | 14 ± 10 |
| 20 | Boc-Leu-Aib-Val-Gly-Aib-Val-Val-Ile-Aib-Thr(OBz)-Val-Aib-Val-Ile-Aib-OMe | 16 ± 7 |
| 21 | Boc-Gly-Leu-Aib-Val-Gly-Aib-Val-Val-Ile-Aib-Thr(OBz)-VaI-Aib-Val-Ile-Aib-OMe | 26 ± 21 |

Aib, aminoisobutyric acid; Ala, alanine; Boc, t-butyloxycarbonyl; BPA, 4-benzoylphenylalanine; Gly, glycine; Ile, isoleucine; Leu, leucine; Met, methionine; OBz, O-benzyl ester; OMe, O-methyl ester; Thr, threonine; and Val, valine.
[a] Asterisks indicate γ-secretase cleavage sites in APP.
[b] Every α-stereocenter has the L-configuration.
[c] Every α-stereocenter has the D-configuration.
[d] Each value was calculated from at least three independent experiments and represents the concentration required for 50% inhibition of Aβ$_{40}$ production.
[e] Ref. 22.

The present results demonstrate that helical peptides can be highly potent γ-secretase inhibitors. Compound with SEQ ID NO:18, with a subnanomolar $IC_{50}$, appears to be among the 9. Duff, K., et al. (1996) *Nature* 383:710-3.
10. Scheuner, D., et al. (1996) *Nat Med* 2:864-70.
11. Wolfe, M. S., et al. (1998) *J Med Chem* 41:6-9.

12. Wolfe, M. S., et al. (1999) *Biochemistry* 38:4720-7.
13. Moore, C. L., et al. (2000) *J Med Chem* 43:3434-42.
14. Lichtenthaler, S. F., et al. (1999) *Proc Natl Acad Sci USA* 96:3053-8.
15. Wolfe, M. S., et al. (1999) *Nature* 398:513-7.
16. Esler, W. P., et al. (2000) *Nature Cell Biology* 2:428-34.
17. Li, Y. M., et al. (2000) *Nature* 405:689-94.
18. Esler, W. P., et al. (2002) *Proc Natl Acad Sci USA* 99:2720-5.
19. Karle, I. L., et al. (1990) *Biochemistry* 29:6747-56.
20. Karle, I. L. (1996) *Biopolymers* 40:157-80.
21. Wenschuh, H., et al. (1995) *J Org Chem* 60:405-10.
22. Das, C., et al. (2003) *J Am Chem Soc* 125:11794-5.
23. Miranda, L. P., et al. (1999) *Proc Natl Acad Sci USA* 96:1181-6.
24. Wenschuh, H., et al. (1994) *J Org Chem* 59:3275-80.
25. Milington, C. R., et al. (1998) *Tetrahedron Letters* 39:7201-4.

All of the references, patents and patent publications identified or cited herein are incorporated, in their entirety, herein by reference.

Although this invention has been described with respect to specific embodiments, the details of these embodiments are not to be construed as limitations. Various equivalents, changes and modifications can be made without departing from the spirit and scope of this invention, and it is understood that such equivalent embodiments are part of this invention.

I claim:

1. A compound of formula:

$$R1-(R2)_n-R3$$

wherein:
- R1 is selected from the group consisting of an acyl, an alkoxycarbonyl, and an aminocarbonyl;
- (R2)$_n$ is an oligomer of n amino acids R2, each selected independently of any other;
- each R2 is independently an achiral, L- or D-amino acid;
- n is an integer from 11 to 16, inclusive; and
- R3 is selected from the group consisting of a hydroxyl, an alkoxyl, an aryloxyl, an amino, an aminoalkyl, and an aminoaryl; and
- wherein (R2)$_n$ comprises at least one dipeptide that mimics a secretase cleavage site in an amyloid precursor protein (APP), wherein at least one said dipeptide is aminoisobutyric acid-O-benzyl threonine (Aib-Thr(OBz)); and
- wherein the compound assumes a substantially helical conformation in solution.

2. The compound of claim 1, wherein at least one said dipeptide is selected from the group consisting of:
Ala-Thr;
Val-Ile;
Ala-R4 wherein R4 is a hydrophobic amino acid;
Ala-R4 wherein R4 is selected from the group consisting of glycine, alanine, valine, isoleucine, phenylalanine, 4-benzoylphenylalanine, and tryptophan;
Ala-R4 wherein R4 is a hydrophilic amino acid;
Ala-R4 wherein R4 is selected from the group consisting of serine and threonine;
Ala-O-benzyl threonine;
Val-R5 wherein R5 is a bulky hydrophobic amino acid;
Val-R5 wherein R5 is selected from the group consisting of isoleucine, leucine, and phenylalanine;
R6-Ile wherein R6 is a bulky hydrophobic amino acid; and
R6-Ile wherein R6 is selected from the group consisting of isoleucine, leucine, and phenylalanine.

3. The compound of claim 1, wherein at least one said dipeptide is Val-R5, and wherein R5 is a bulky hydrophobic amino acid.

4. The compound of claim 3, wherein R5 is selected from the group consisting of isoleucine, leucine, and phenylalanine.

5. The compound of claim 1, wherein at least one said dipeptide is R6-Ile, and wherein R6 is a bulky hydrophobic amino acid.

6. The compound of claim 5, wherein R6 is selected from the group consisting of isoleucine, leucine, and phenylalanine.

7. The compound of claim 1, wherein at least one said dipeptide is Val-Ile.

8. The compound of claim 1, wherein at least one R2 is an L-amino acid.

9. The compound of claim 1, wherein at least one R2 is a D-amino acid.

10. The compound of claim 1, wherein at least one R2 is a hydrophobic amino acid.

11. The compound of claim 10, wherein the hydrophobic amino acid is selected from the group consisting of glycine, alanine, valine, isoleucine, leucine, phenylalanine, 4-benzoylphenylalanine, and tryptophan.

12. The compound of claim 1, wherein at least one R2 is a hydrophilic amino acid.

13. The compound of claim 12, wherein the hydrophilic amino acid is selected from the group consisting of serine and threonine.

14. The compound of claim 1, wherein at least one additional R2 is aminoisobutyric acid (Aib).

15. A compound is selected from the group consisting of:
Boc-Aib-Val-Val-Ile-Aib-Thr(OBz)-Val-Aib-Val-Ile-Aib-OMe (SEQ ID NO: 16),
Boc-Gly-Aib-Val-Val-Ile-Aib-Thr(OBz)-Val-Aib-Val-Ile-Aib-OMe (SEQ ID NO: 17),
Boc-Val-Gly-Aib-Val-Val-Ile-Aib-Thr(OBz)-Val-Aib-Val-Ile-Aib-OMe (SEQ ID NO:18),
Boc-Aib-Val-Gly-Aib-Val-Val-Ile-Aib-Thr(OBz)-Val-Aib-Val-Ile-Aib-OMe (SEQ ID NO:19),
Boc-Leu-Aib-Val-Gly-Aib-Val-Val-Ile-Aib-Thr(OBz)-Val-Aib-Val-Ile-Aib-OMe (SEQ ID NO:20), and
Boc-Gly-Leu-Aib-Val-Gly-Aib-Val-Val-Ile-Aib-Thr(OBz)-Val-Aib-Val-Ile-Aib-OMe (SEQ ID NO:21),
wherein Boc is t-butyloxycarbonyl;
wherein OBz is O-benzyl ester;
wherein OMe is O-methyl ester;
wherein Aib is aminoisobutyric acid; and
optionally wherein at least one of the amino acid is a D-amino acid.

16. The compound of claim 15, wherein at least one of the amino acids is a D-amino acid.

17. The compound of claim 15, wherein at least one of the amino acids is an L-amino acid.

18. The compound of claim 15, wherein each and every chiral amino acid is a D-amino acid.

19. The compound of claim 15, wherein each and every chiral amino acid is an L-amino acid.

20. A pharmaceutically acceptable salt of the compound of claim 1.

21. A composition comprising the compound of claim 1 and a pharmaceutically acceptable carrier.

22. The composition of claim 21, further comprising a carrier to promote delivery to a brain.

23. A compound of formula:

R1-Val-Gly-Aib-Val-Val-Ile-Aib-Thr(OBz)-Val-Aib-Val-Ile-Aib-R3 (SEQ ID NO: 24)

wherein:
R1 is selected from the group consisting of a hydrogen, an acyl, an alkoxycarbonyl, and an aminocarbonyl; and
R3 is selected from the group consisting of a hydroxyl, an alkoxyl, an aryloxyl, an amino, an aminoalkyl, and an aminoaryl.

24. A method of inhibiting an activity of an intramembrane protease, comprising:
contacting an intramembrane protease under conditions in which the intramembrane protease is enzymatically active with an effective amount of a compound of claim 1, to inhibit the activity of the intramembrane protease.

25. A pharmaceutically acceptable salt of the compound of claim 15.

26. A composition comprising the compound of claim 15 and a pharmaceutically acceptable carrier.

27. The composition of claim 26, further comprising a carrier to promote delivery to a brain.

* * * * *

SEQUENCE LISTING

```
<160> NUMBER OF SEQ ID NOS: 23

<210> SEQ ID NO 1
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Ala
<220> FEATURE:
<221> NAME/KEY: MISC_FEATURE
<222> LOCATION: (2)..(2)
<223> OTHER INFORMATION: O-benzyl-Thr
<220> FEATURE:
<221> NAME/KEY: MISC_FEATURE
<222> LOCATION: (3)..(3)
<223> OTHER INFORMATION: Aib
<220> FEATURE:
<221> NAME/KEY: MISC_FEATURE
<222> LOCATION: (6)..(6)
<223> OTHER INFORMATION: O-methyl-Aib

<400> SEQUENCE: 1

Xaa Xaa Xaa Ile Val Xaa
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Ile
<220> FEATURE:
<221> NAME/KEY: MISC_FEATURE
<222> LOCATION: (3)..(3)
<223> OTHER INFORMATION: O-benzyl-Thr
<220> FEATURE:
<221> NAME/KEY: MISC_FEATURE
<222> LOCATION: (4)..(4)
<223> OTHER INFORMATION: Aib
<220> FEATURE:
<221> NAME/KEY: MISC_FEATURE
<222> LOCATION: (7)..(7)
<223> OTHER INFORMATION: O-methyl-Aib
```

-continued

```
<400> SEQUENCE: 2

Xaa Ala Xaa Xaa Ile Val Xaa
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Aib
<220> FEATURE:
<221> NAME/KEY: MISC_FEATURE
<222> LOCATION: (4)..(4)
<223> OTHER INFORMATION: O-benzyl-Thr
<220> FEATURE:
<221> NAME/KEY: MISC_FEATURE
<222> LOCATION: (5)..(5)
<223> OTHER INFORMATION: Aib
<220> FEATURE:
<221> NAME/KEY: MISC_FEATURE
<222> LOCATION: (8)..(8)
<223> OTHER INFORMATION: O-methyl-Aib

<400> SEQUENCE: 3

Xaa Ile Ala Xaa Xaa Ile Val Xaa
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Val
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (5)..(5)
<223> OTHER INFORMATION: O-benzyl-Thr
<220> FEATURE:
<221> NAME/KEY: MISC_FEATURE
<222> LOCATION: (6)..(6)
<223> OTHER INFORMATION: Aib
<220> FEATURE:
<221> NAME/KEY: MISC_FEATURE
<222> LOCATION: (9)..(9)
<223> OTHER INFORMATION: O-methyl-Aib

<400> SEQUENCE: 4

Xaa Xaa Ile Ala Xaa Xaa Ile Val Xaa
1               5

<210> SEQ ID NO 5
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Gly
```

```
<220> FEATURE:
<221> NAME/KEY: MISC_FEATURE
<222> LOCATION: (3)..(3)
<223> OTHER INFORMATION: Aib
<220> FEATURE:
<221> NAME/KEY: MISC_FEATURE
<222> LOCATION: (6)..(6)
<223> OTHER INFORMATION: O-benzyl-Thr
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (10)..(10)
<223> OTHER INFORMATION: O-methyl-Aib

<400> SEQUENCE: 5

Xaa Val Xaa Ile Ala Xaa Xaa Ile Val Xaa
1               5                   10

<210> SEQ ID NO 6
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Val
<220> FEATURE:
<221> NAME/KEY: MISC_FEATURE
<222> LOCATION: (3)..(3)
<223> OTHER INFORMATION: Aib
<220> FEATURE:
<221> NAME/KEY: MISC_FEATURE
<222> LOCATION: (4)..(4)
<223> OTHER INFORMATION: O-benzyl-Thr
<220> FEATURE:
<221> NAME/KEY: MISC_FEATURE
<222> LOCATION: (6)..(6)
<223> OTHER INFORMATION: O-methyl Aib

<400> SEQUENCE: 6

Xaa Ile Xaa Xaa Val Xaa
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Val
<220> FEATURE:
<221> NAME/KEY: MISC_FEATURE
<222> LOCATION: (4)..(4)
<223> OTHER INFORMATION: Aib
<220> FEATURE:
<221> NAME/KEY: MISC_FEATURE
<222> LOCATION: (5)..(5)
<223> OTHER INFORMATION: O-benzyl-Thr
<220> FEATURE:
<221> NAME/KEY: MISC_FEATURE
<222> LOCATION: (7)..(7)
<223> OTHER INFORMATION: O-methyl-Aib

<400> SEQUENCE: 7

Xaa Val Ile Xaa Xaa Val Xaa
1               5
```

```
<210> SEQ ID NO 8
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Aib
<220> FEATURE:
<221> NAME/KEY: MISC_FEATURE
<222> LOCATION: (5)..(5)
<223> OTHER INFORMATION: Aib
<220> FEATURE:
<221> NAME/KEY: MISC_FEATURE
<222> LOCATION: (6)..(6)
<223> OTHER INFORMATION: O-benzyl-Thr
<220> FEATURE:
<221> NAME/KEY: MISC_FEATURE
<222> LOCATION: (8)..(8)
<223> OTHER INFORMATION: O-methyl-Aib

<400> SEQUENCE: 8

Xaa Val Val Ile Xaa Xaa Val Xaa
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Gly
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (6)..(6)
<223> OTHER INFORMATION: Aib
<220> FEATURE:
<221> NAME/KEY: MISC_FEATURE
<222> LOCATION: (7)..(7)
<223> OTHER INFORMATION: O-benzyl-Thr
<220> FEATURE:
<221> NAME/KEY: MISC_FEATURE
<222> LOCATION: (9)..(9)
<223> OTHER INFORMATION: O-methyl-Aib

<400> SEQUENCE: 9

Xaa Xaa Val Val Ile Xaa Xaa Val Xaa
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Val
<220> FEATURE:
<221> NAME/KEY: MISC_FEATURE
<222> LOCATION: (3)..(3)
<223> OTHER INFORMATION: Aib
```

```
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (8)..(8)
<223> OTHER INFORMATION: O-benzyl-Thr
<220> FEATURE:
<221> NAME/KEY: MISC_FEATURE
<222> LOCATION: (10)..(10)
<223> OTHER INFORMATION: O-methyl-Aib

<400> SEQUENCE: 10

Xaa Gly Xaa Val Val Ile Xaa Xaa Val Xaa
 1               5                  10

<210> SEQ ID NO 11
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Val
<220> FEATURE:
<221> NAME/KEY: MISC_FEATURE
<222> LOCATION: (3)..(3)
<223> OTHER INFORMATION: Aib
<220> FEATURE:
<221> NAME/KEY: MISC_FEATURE
<222> LOCATION: (6)..(6)
<223> OTHER INFORMATION: 4-benzoyl-Thr
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (8)..(8)
<223> OTHER INFORMATION: O-benzyl-Thr
<220> FEATURE:
<221> NAME/KEY: MISC_FEATURE
<222> LOCATION: (10)..(10)
<223> OTHER INFORMATION: O-methyl-Aib

<400> SEQUENCE: 11

Xaa Gly Xaa Val Val Xaa Xaa Xaa Val Xaa
 1               5                  10

<210> SEQ ID NO 12
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Partial sequence - amyloid precursor protein
<220> FEATURE:
<221> NAME/KEY: SITE
<222> LOCATION: (5)..(6)
<223> OTHER INFORMATION: Gamma secretase cleavage site
<220> FEATURE:
<221> NAME/KEY: SITE
<222> LOCATION: (7)..(8)
<223> OTHER INFORMATION: Gamma secretase cleavage site

<400> SEQUENCE: 12

Val Gly Gly Val Val Ile Ala Thr Val Ile Val Ile
 1               5                  10
```

```
<210> SEQ ID NO 13
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Aib
<220> FEATURE:
<221> NAME/KEY: MISC_FEATURE
<222> LOCATION: (4)..(4)
<223> OTHER INFORMATION: Aib
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (10)..(10)
<223> OTHER INFORMATION: O-methyl-Aib

<400> SEQUENCE: 13

Xaa Ala Leu Xaa Ala Leu Xaa Ala Leu Xaa
1               5                   10

<210> SEQ ID NO 14
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Aib
<220> FEATURE:
<221> NAME/KEY: MISC_FEATURE
<222> LOCATION: (6)..(6)
<223> OTHER INFORMATION: Aib
<220> FEATURE:
<221> NAME/KEY: MISC_FEATURE
<222> LOCATION: (7)..(7)
<223> OTHER INFORMATION: Ile-ol

<400> SEQUENCE: 14

Ile Ile Xaa Ile Ile Xaa Xaa
1               5

<210> SEQ ID NO 15
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Val
<220> FEATURE:
<221> NAME/KEY: MISC_FEATURE
<222> LOCATION: (4)..(4)
<223> OTHER INFORMATION: Aib
<220> FEATURE:
<221> NAME/KEY: MISC_FEATURE
<222> LOCATION: (5)..(5)
<223> OTHER INFORMATION: O-benzyl-Thr
```

```
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (10)..(10)
<223> OTHER INFORMATION: O-methyl-Aib

<400> SEQUENCE: 15

Xaa Val Ile Xaa Xaa Val Xaa Val Ile Xaa
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Aib
<220> FEATURE:
<221> NAME/KEY: MISC_FEATURE
<222> LOCATION: (5)..(5)
<223> OTHER INFORMATION: Aib
<220> FEATURE:
<221> NAME/KEY: MISC_FEATURE
<222> LOCATION: (6)..(6)
<223> OTHER INFORMATION: O-benzyl-Thr
<220> FEATURE:
<221> NAME/KEY: MISC_FEATURE
<222> LOCATION: (8)..(8)
<223> OTHER INFORMATION: Aib
<220> FEATURE:
<221> NAME/KEY: MISC_FEATURE
<222> LOCATION: (11)..(11)
<223> OTHER INFORMATION: O-methyl-Aib

<400> SEQUENCE: 16

Xaa Val Val Ile Xaa Xaa Val Xaa Val Ile Xaa
1               5                   10

<210> SEQ ID NO 17
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Gly
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (6)..(6)
<223> OTHER INFORMATION: Aib
<220> FEATURE:
<221> NAME/KEY: MISC_FEATURE
<222> LOCATION: (7)..(7)
<223> OTHER INFORMATION: O-benzyl-Thr
<220> FEATURE:
<221> NAME/KEY: MISC_FEATURE
<222> LOCATION: (9)..(9)
<223> OTHER INFORMATION: Aib
<220> FEATURE:
<221> NAME/KEY: MISC_FEATURE
<222> LOCATION: (12)..(12)
<223> OTHER INFORMATION: O-methyl-Aib
```

-continued

```
<400> SEQUENCE: 17

Xaa Xaa Val Val Ile Xaa Xaa Val Xaa Val Ile Xaa
1               5                   10

<210> SEQ ID NO 18
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Val
<220> FEATURE:
<221> NAME/KEY: MISC_FEATURE
<222> LOCATION: (3)..(3)
<223> OTHER INFORMATION: Aib
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (8)..(8)
<223> OTHER INFORMATION: O-benzyl-Thr
<220> FEATURE:
<221> NAME/KEY: MISC_FEATURE
<222> LOCATION: (10)..(10)
<223> OTHER INFORMATION: Aib
<220> FEATURE:
<221> NAME/KEY: MISC_FEATURE
<222> LOCATION: (13)..(13)
<223> OTHER INFORMATION: O-methyl-Aib

<400> SEQUENCE: 18

Xaa Gly Xaa Val Val Ile Xaa Xaa Val Xaa Val Ile Xaa
1               5                   10

<210> SEQ ID NO 19
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Aib
<220> FEATURE:
<221> NAME/KEY: MISC_FEATURE
<222> LOCATION: (4)..(4)
<223> OTHER INFORMATION: Aib
<220> FEATURE:
<221> NAME/KEY: MISC_FEATURE
<222> LOCATION: (8)..(8)
<223> OTHER INFORMATION: Aib
<220> FEATURE:
<221> NAME/KEY: MISC_FEATURE
<222> LOCATION: (9)..(9)
<223> OTHER INFORMATION: O-benzyl-Thr
<220> FEATURE:
<221> NAME/KEY: MISC_FEATURE
<222> LOCATION: (11)..(11)
<223> OTHER INFORMATION: Aib
<220> FEATURE:
<221> NAME/KEY: MISC_FEATURE
<222> LOCATION: (14)..(14)
<223> OTHER INFORMATION: O-methyl-Aib

<400> SEQUENCE: 19

Xaa Val Gly Xaa Val Val Ile Xaa Xaa Val Xaa Val Ile Xaa
1               5                   10
```

<210> SEQ ID NO 20
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Leu
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (5)..(5)
<223> OTHER INFORMATION: Aib
<220> FEATURE:
<221> NAME/KEY: MISC_FEATURE
<222> LOCATION: (9)..(9)
<223> OTHER INFORMATION: Aib
<220> FEATURE:
<221> NAME/KEY: MISC_FEATURE
<222> LOCATION: (10)..(10)
<223> OTHER INFORMATION: O-benzyl-Thr
<220> FEATURE:
<221> NAME/KEY: MISC_FEATURE
<222> LOCATION: (12)..(12)
<223> OTHER INFORMATION: Aib
<220> FEATURE:
<221> NAME/KEY: MISC_FEATURE
<222> LOCATION: (15)..(15)
<223> OTHER INFORMATION: O-methyl-Aib

<400> SEQUENCE: 20

Xaa Xaa Val Gly Xaa Val Val Ile Xaa Xaa Val Xaa Val Ile Xaa
1               5                   10                  15

<210> SEQ ID NO 21
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: t-butyloxycarbonyl-Gly
<220> FEATURE:
<221> NAME/KEY: MISC_FEATURE
<222> LOCATION: (3)..(3)
<223> OTHER INFORMATION: Aib
<220> FEATURE:
<221> NAME/KEY: MISC_FEATURE
<222> LOCATION: (6)..(6)
<223> OTHER INFORMATION: Aib
<220> FEATURE:
<221> NAME/KEY: MISC_FEATURE
<222> LOCATION: (10)..(10)
<223> OTHER INFORMATION: Aib
<220> FEATURE:
<221> NAME/KEY: MISC_FEATURE
<222> LOCATION: (11)..(11)
<223> OTHER INFORMATION: O-benzyl-Thr
<220> FEATURE:
<221> NAME/KEY: MISC_FEATURE
<222> LOCATION: (13)..(13)
<223> OTHER INFORMATION: Aib
<220> FEATURE:
<221> NAME/KEY: MISC_FEATURE
<222> LOCATION: (16)..(16)
<223> OTHER INFORMATION: O-methyl-Aib

```
<400> SEQUENCE: 21

Xaa Leu Xaa Val Gly Xaa Val Val Ile Xaa Xaa Val Xaa Val Ile Xaa
1               5                   10                  15

<210> SEQ ID NO 22
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: Partial sequence - amyloid precursor protein
<220> FEATURE:
<221> NAME/KEY: SITE
<222> LOCATION: (8)..(9)
<223> OTHER INFORMATION: Gamma secretase cleavage site
<220> FEATURE:
<221> NAME/KEY: SITE
<222> LOCATION: (10)..(11)
<223> OTHER INFORMATION: Gamma secretase cleavage site

<400> SEQUENCE: 22

Gly Leu Met Val Gly Gly Val Val Ile Ala Thr Val Ile Val Ile Thr
1               5                   10                  15

<210> SEQ ID NO 23
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Aib
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (8)..(8)
<223> OTHER INFORMATION: O-benzyl-Thr
<220> FEATURE:
<221> NAME/KEY: MISC_FEATURE
<222> LOCATION: (10)..(10)
<223> OTHER INFORMATION: Aib
<220> FEATURE:
<221> NAME/KEY: MISC_FEATURE
<222> LOCATION: (13)..(13)
<223> OTHER INFORMATION: Aib-amide

<400> SEQUENCE: 23

Val Gly Xaa Val Val Ile Xaa Xaa Val Xaa Val Val Xaa
1               5                   10
```